(12) United States Patent
Kish et al.

(10) Patent No.: US 9,377,530 B2
(45) Date of Patent: Jun. 28, 2016

(54) ECHOLOCATION SYSTEMS AND METHODS

(71) Applicant: World Access for the Blind, Placentia, CA (US)

(72) Inventors: Daniel Kish, Placentia, CA (US); Derik DeVecchio, Placentia, CA (US)

(73) Assignee: World Access for the Blind, Placentia, CA (US)

( * ) Notice: Subject to any disclaimer, the term of this patent is extended or adjusted under 35 U.S.C. 154(b) by 483 days.

(21) Appl. No.: 13/803,731

(22) Filed: Mar. 14, 2013

(65) Prior Publication Data

US 2014/0269189 A1 Sep. 18, 2014

(51) Int. Cl.
*A61H 3/06* (2006.01)
*G01S 15/88* (2006.01)
*G01S 7/534* (2006.01)
*A61F 9/08* (2006.01)

(52) U.S. Cl.
CPC .............. *G01S 15/88* (2013.01); *A61H 3/061* (2013.01); *G01S 7/534* (2013.01); *A61F 9/08* (2013.01); *A61H 2003/065* (2013.01); *A61H 2201/165* (2013.01); *A61H 2201/5097* (2013.01)

(58) Field of Classification Search
CPC ... G01S 15/88; G01S 7/534; A61H 2003/065; A61H 2210/165; A61H 3/061; A61F 9/08
USPC ........................................... 340/4.1; 367/116
See application file for complete search history.

(56) References Cited

U.S. PATENT DOCUMENTS

| | | | | |
|---|---|---|---|---|
| 4,761,770 A * | 8/1988 | Kim et al. | ...................... | 367/116 |
| 5,107,467 A * | 4/1992 | Jorgensen et al. | ............ | 367/116 |
| 6,011,754 A * | 1/2000 | Burgess et al. | ............... | 367/116 |
| 7,957,224 B2 * | 6/2011 | Tremper | ...................... | 367/116 |
| 2002/0154161 A1* | 10/2002 | Friedman et al. | ............. | 345/740 |
| 2008/0058894 A1* | 3/2008 | Dewhurst | ........................ | 607/54 |
| 2009/0286211 A1* | 11/2009 | Eisenhardt et al. | ........... | 434/113 |

OTHER PUBLICATIONS

Arnott, S. et al., Shape-specific activation of occipital cortex in an early blind echolocation expert, Neuropsychologia, Jan. 2013, web page at http://dx.doi.org/10.1016/j.neuropsychologia.2013.01.024, as available via the Internet.

(Continued)

*Primary Examiner* — Luke Ratcliffe
*Assistant Examiner* — Hovhannes Baghdasaryan
(74) *Attorney, Agent, or Firm* — Kilpatrick Townsend & Stockton LLP

(57) ABSTRACT

An echolocation device assists visually impaired persons to navigate their environment. The echolocation device comprises a micro control unit, a power source operably connected to the micro control unit, a band pass preamplifier operably connected to the micro control unit, a power amplifier operably connected to the band pass preamplifier, a piezoelectric speaker operably connected to the power amplifier, and a user interface operably connected to the micro control unit. The device emits sound waves that echo off nearby surrounding objects. The visually impaired person listens to the echoes to determine the location or size of the surrounding objects.

22 Claims, 8 Drawing Sheets

(56) References Cited

OTHER PUBLICATIONS

Bazley, N., For blind and visually impaired people there are some common tricks used to get around like canes. But have you seen anyone use the skills of a bat to do the same thing? You're about to meet a blind man who uses bat-like sonar skills to be able to 'see'. He's become so good at it he's holding a series of workshops with blind Australian students to help improve their skills, Behind the News—Batman, Episode 3, Feb. 2012, web page at www.abc.net.au/btn/story/s3440826.htm, as available via the internet.

Blesser, B. et al., Spaces speak, are you listening? Experiencing Aural Architecture, MIT Press, 2007, web page at www. blesser.net/spacesSpeak.html, as available via the Internet, pp. 1-7.

Brown, The power of perception—how human echolocation is being put into practice, Mountain Bike Action Magazine, Spring 2011, pp. 13-14.

Chung, E., Blind people echolocate with visual part of brain, CBC News, May 2011, web page at www.cbc.ca/news/technology/blind-people-echolocate-with-visual-part-of-brain-1.1012642,a s available via the Internet. pp. 1-12.

Cytowic, R. et al., Extraordinary secrets of our linked-up senses, New Scientist, Apr. 2010, web page at www.newscientist.com/blogs/culturelab/2010/04/extraordinary-secrets-of-our-linked-up-senses.html, as available via the Internet, pp. 1-4.

Downey, G., Getting around by sound: human echolocation, PLOS Journals, PLOS Blogs, Dec. 2013, web page at blogs.plos.org/neuroanthropology/2011/06/14/getting-around-by-sound-human-echolocation, as available via the Internet, pp. 1-23.

Erin, J., Practice perspectives traveling by touch? How useful are tactile maps? Journal of Visual Impairment and Blindness, May 2009, vol. 103, No. 5, 6 pgs.

Finkel, M., The blind man who taught himself to see, Men's Journal Magazine, Mar. 2011, web page at www.mensjournal.com/article/print-view/the-blind-man-who-taught-himself-to-see-20120504, as available via the Internet, 9 pages.

Fernandez, C. et al., How the blind could be taught to see like a bat using new echo technique, mail Online, Feb. 2008, web page at www.dailymail.co.uk/news/article-513449/How-blind-taught-like-bat-using-new-echo-technique.html?printingPage=true, available via the Internet, 2 pages.

Grandy, J., The explosion of consciousness: TSC Conference Tucson Arizona 2012, Journal of Consciousness Exploration & Research, May 2012, vol. 3, Issue 4, pp. 432-445.

Groeger, L., Making sense of the world, several senses at a time, Scientific American, Feb. 2012, web page at www.scientificamerican.com/article.cfm?id=making-sense-world-sveral-senses-at-time, as available via the Internet, 7 pages.

Gupta, S. et al., Seeing with sound, CNN.com Transcripts, Dec. 2011, web page at transcripts.cnn.com/TRANSCRIPTS/1112/10/hcsg.01.html, as available via the Internet, 5 pages.

Kish, D., When darkness lights the way: how the blind may function as specialists in movement and navigation, World Access for the Blind Inc., Copyright 2003.

Kish, D., Echo vision: the man who sees with sound, Health and Wellness—Sott.net, Apr. 2009, web page at www.sott.net/article/181775-Echo-vision-The-man-who-sees-with-sound, as available via the Internet, 4 pages.

Kish, D., Echolocation: How humans can "see" without sight, Master Thesis, California State University, 1995, 45 pages.

Kish, D., Sonic Echolocation: a modern review and synthesis of the literature, World Access for the Blind, Copyright 2003, web page at www.worldaccessfortheblind.org/sites/default/files/echolocationreview.htm, as available via the Internet, 55 pages.

Kish, D., Embracing our world, World Access for the Blind, Copyright 2003, web page at www.worldaccessfortheblind.org/sites/default/files/embrace2003a.htm, as available via the Internet, 161 pages.

Kish, D., Experience:I taught myself to see, The Guardian, Jul. 2013, web page at www.theguardian.com/lifeandstyle/2013/jul/13/experience-blindness-echolocation-daniel-kish, as available via the Internet, 4 pages.

Kish, D. et al., Facilitating movement and navigation in blind preschoolers: a positive, practical approach, Association for the education and Rehabilitation of the Blind and Visually Impaired 1998 Conferences, 19 pages.

Kish, D., Flashsonar: understanding and applying sonar imaging to mobility, Future Reflections, Winter 2011, web page at https://nfb.org/images/nfb/publications/fr/fr30/1/fr300107.htm, as available via the Internet, 8 pages.

Kish, D., Flash sonar mobility skills training in South Africa, SA National Council for the Blind, 2010, web page at www.sancb.org.za/article/flash-sonar-mobility-skills-training-south-africa-daniel-kish, as available via the Internet, 3 pages.

Kish, D., Echovision: the man who sees with sound, New Scientist, Apr. 2009, web page at www.newscientist.com/article/mg20227031.400-echo-vision-the-man-who-sees-with-sound.html?full=true, as available via the Internet, 2 pages (Abstract).

Kish, D., A Perception basis for cane length considerations, Association for Education and Rehabilitation of the Blind and Visually Impaired, AER Report, vol. 26, No. 1, 2009, web page at www.worldaccessfortheblind.org/sites/default/files/AER_Article_1.htm, as available via the Internet, 3 pages.

Kish, D. et al., Flashsonar; the next step in echolocation instruction, Association for Education and Rehabilitation of the Blind and Visually Impaired, AER Report, vol. 26, No. 2, 2009, web page at www.worldaccessfortheblind.org/sites/default/files/AER_Article_2.htm, as available via the Internet, 3 pages.

Kish, D., Flash sonar program: learning a new way to see, World Access for the Blind, Copyright 2013, web page at www.worldaccessfortheblind.org/sites/default/filed/snr-pgm-rv1113.htm, as available via the Internet, 45 pages.

Kish, D., Self-directed achievement, perceptual development, and flashsonar: how blind people can learn to see without sight, World Access for the Blind, Mar. 2009, web page at www.worldaccessfortheblind.org/sites/default/files/sonrwrkshop2d.txt, as available via the Internet, 8 pages.

Langille, J., Echolocation helps blind people navigate everyday life, Jane Langille, Sep. 2012, web page at janelangille.com/echolocation-helps-blind-people-navigate-everyday-life, as available via the Internet, 7 pages.

Lin, T., Hitting the court, with an ear on the ball—A game of tennis tests notions of blindness, Science, the NY Times, Jun. 2012, web page at www.nytimes.com/2012/06/05/science/a-game-of-tennis-test-notions-of-blindness.html?_r=1&, as available via the Internet, 4 pages.

Lombrozo, T., Be like a bat? Sound can show you the way, NPR 13.7 Cosmos & Culture, Jan. 2013, web page at www.npr.org/blogs/13.7/2013/01/28/170355712/be-like-a-bat-sound-can-show-you-the-way, as available via the Internet, 6 pages.

Mac, R., Soccer no obstacle to blind children, The Orange County Register, Jul. 2010, web page at www.ocregister.com/news/blind-258231-soccer-ball.html, as available via the Internet, 3 pages.

Markovich, J., Blind Faith, Charlotte Magazine, Jan. 2009, web page at www.charlottemagazine.com/Charlotte-Magazine/January-2009/Blind-Faith, as available via the Internet, 4 pages.

Markovich, J., Blind hiker Trevor Thomas takes the pacific coast trail, Charlotte Magazine, Oct. 2010, web page at www.charlottemagazine.com/Charlotte-Magazine/October-2010/Blind-Hiker-Trevor-Thomas-Takes-the-Pacific-Coast-Trail, as available via the Internet, 2 pages.

McIlroy, A., Radar-like 'inner-vision' helps blind learn to navigate beyond preconceived limits, The Globe and Mail, May 2011, web page at www.theglobeandmail.com/technology/science/radar-like-inner-vision-helps-blind-learn-to-navigate-beyond-preconceived-limits/article598412, as available via the Internet, 2 pages.

Moisse, K., Like a bat, blind man uses sound to 'see', ABC News via Good Morning America, May 2011, web page at abcnews.go.com/Health/MindMoodNews/blind-man-echolocation/story?id=13684073, as available via the Internet, 4 pages.

(56) References Cited

OTHER PUBLICATIONS

Oxley, N., Transcript of RNIB echolocation Podcast, Nov. 2008, 6 pages.
Ramirez, M., Eight-year-old Lewisville boy destined for blindness learns some new tricks, Jun. 2011, Dallas News, 5 pages.
Ravilious, K., Humans can learn to 'see' with sound, study says, National Geographic News, Jul. 2009, web page at news.nationalgeographic.com/news/2009/07/090706-humans-bats-echolocation.html, as available via the Internet, 2 pages.
Reed, S., The blind leading the blind—an eye opening experience, The Orange County Register, Sep. 2010, web page at www.ocregister.com/articles/blind-267255-echolocation-new.html, as available via the Internet, 3 pages.
Rojas, J. et al., Physical analysis of several organic signals for human echolocation: oral vacuum pulses, Department of Signal Theory and Communication, Universidad of Alcala, Escuela Politencnica Superior, Campus Universitario, Ctra. De Madrid—Barcelona, Spain, Sep. 2008.
Rojas, J. et al., Physical analysis of several organic signals for human echolocation: hand and finger produced pulses, Department of Signal Theory and Communication, Universidad of Alcala, Escuela Politencnica Superior, Campus Universitario, Ctra. De Madrid—Barcelona, Spain, Mar. 2010.
Rosenblum, L., Mountain biking with the blind, Psychology Today, Jul. 2009, web page at www.psychologytoday.com/blog/sensory-superpowers/200907/mountain-biking-the-blind, as available via the Internet, 3 pages.
Schorn, D., How a blind teen 'sees' with sound, CBS News, Jul. 2006, web site at www.cbsnews.com/news/how-a-blind-teen-sees-with-sound, as available via the Internet, 3 pages.
Schornich, S. et al., Psychophysics of human echolocation, Adv. Exp. Med. Biol., 2013, vol. 787, pp. 311-319.
Seraphin, A., Echolocation Woodstock, Austin Seraphin's Weird Blog, May 2012, web page at behindthecurtain.us/2012/05/08/echolocation-woodstock, as available via the Internet, 7 pages.
Seraphin, A., Echolocation sculpture: a monument to abstraction, Austin Seraphin's Weird Blog, Oct. 2012, web page at blog.austinseraphin.com/2012/10/27/echolocating-sculpture-a-monument-to-abstraction, as available via the Internet, 6 pages.
Seraphin, A., Seeing with sound, a piece about echolocation, Austin Seraphin's Weird Blog, Jul. 2013, web page at blog.austinseraphin.com/2013/07/27/seeing-with-sound-a-piece-about-echolocation, as available via the Internet, 4 pages.
Shea, C., Echolocation in humans, Ideas Market—WSJ Blogs, May 2011, web page at blogs.wsj.com/ideas-market/2011/05/25/echolocation-in-humans, as available via the Internet, 3 pages.
Sher, J., Blind 'batman' teaches others to see, QMI Agency, Jun. 2011, 2 pages.
Sher, J., Medical marvel, QMI Agency, Jun. 2011, 3 pages.
Sterne, J. et al., The recording that never wanted to be heard and other stories of sonification, The Oxford Handbook of Sound Studies, Bijsterveld and Pinch, Eds., Nov. 2012, 27 pages.
Sutter, J., Blind man uses ears to see, Cnn.com, Nov. 2011, web page at 0-www.cnn.com.library.ccbcmd.edu/2011/11/09/tech/innovation/daniel-kish-poptech-echolocation/index.html#ContentArea, as available via the Internet, 8 pages.
Teng, S. et al., The acuity of echolocation: spatial resolution in the sighted compared to expert performance, NIH Public Access, J Vis Impair Blind. Author manuscript; available in PMC May 2011, 15 pages.
Thaler, L., Echolocation may have real-life advantages for blind people: an analysis of survey data, Frontiers in Physiology, May 2013, web page at www.frontiersin.org/Integrative_Physiology/10.3389/fphys.2013.00098/full, as available via the Internet, 9 pages.
Thaler, L. et al., Neural correlates of natural human echolocation in early and late blind echolocation experts, PLos ONE, May 2011, vol. 6, No. 5, 16 pages.
Travis, H., Seeing through sound: how a tongue click gave one man independence, The University of Western News, May 2011, web page at communications.uwo.ca/western_news/stories/2011/May/seeing_through_sound_how_a_tongue_click_gave_one_man_independence.html, as available via the Internet, 6 pages.
Walters, P., Risk Takers, National Geographic Magazine, web page atngm.nationalgeographic.com/125-exploration/risk-takers-gallery#/1, as avaialbe via the Internet and printed Dec. 2013, 13 pages.
Whittington, M. et al., Human echolocation, Yahoo Voices, Oct. 2006, web page at http://www.voices.yahoo.com/human-echolocation-100063.html, as available via the Internet, 3 pages.
Williams, C., Crittervision: enter the bat's world of sound, New Scientist, Aug. 2011, web page atwww.newscientist.com/article/mg21128261.900-crittervision-enter-the-bats-world-of-sound.html#.Uqi3IfRDtnB, as available via the Internet, 3 pages.
Wysong, P., Seeing by ear, Eurotimes, vol. 16, Issue 10, Oct. 2011, web page at escrs.org/publications/EUROTIMES/11October/seeingbyear.pd.
Yong, E., The brain on sonar—how blind people find their way around with echoes, Not Exactly Rocket Science, May 2011, web page at blogs.discovermagazine.com/notrocketscience/2011/05/25/the-brain-on-sonar-how-blind-people-find-their-way-around-with-echoes/#.Uqi2vPRDtnA, as available via the Internet, 5 pages.
"Zen" bats hit their target by not aiming at it! University Communications Newsdesk, University of Maryland, Feb. 2010, web page at www.newsdesk.umd.edu/scitech/release.cfm?ArticleID=2078, as available via the Internet, 2 pages.
Sound Affects, Whale & Dolphin, Winter 2013, 3 pages.
Sensory integration and praxis pre-conference institute, R2K Research 2011—Building bridges between research and practice, Feb. 25-26, 2011.
Blind ambition leads to bike club, Daily News (Los Angeles, CA) via the Free Library, Sep. 2002, web page at www.thefreelibrary.com/BLIND+AMBITION+LEADS+TO+BIKE+CLUB.-a092172643, as available via the Internet, 3 pages.
Blind people may be able to use echoes to identify objects, US News and World Report, May 2011, web page at health.usnews.com/health-news/family-health/brain-and-behavior/articles/2011/05/26/blind-people-may-be-able-to-use-echoes-to-identify-objects, as available via the Internet, 1 page.
Blindness no obstacle to those with sharp ears, NPR, Mar. 2011, web page at www.npr.org/2011/03/13/134425825/human-echolocation-using-sound-to-see?live=1, as available via the Internet, 3 pages.
Echolocation in humans—seminar and demonstration, CIN 2010 Events, Jul. 2010, web page at www.cin.uni-tuebingen.de/events/past-events/2010-events.php#event_47, as available via the Internet, 6 pages (abstract only).
Camp helps kids get a kick out of soccer, Daily Breeze, Jun. 2011, web page at www.dailybreeze.com/general-news/20110618/camp-helps-kids-get-a-kick-out-of-soccer, as available via the Internet, 11 pages.
Interview with Daniel Kish, Daredevil: The Man without Fear, Mar. 2004, web page at www.manwithoutfear.com/daredevil-interviews/Kish, as available via the Internet, 4 pages.
Daniel Kish and activating neural hardware, Neuropickings, epilepsy straight from the head, Aug. 2013, web page at neuropickings.wordpress.com/2013/08/07/daniel-kish-and-activating-neural-hardware, as available via the Internet, 5 pages.
Daniel Kish Interview—Vijay wanted to know how I live my life, Behindwoods, web page at behindwoods.com/new-videos/tamil-actors/daniel-kish/daniel-kish-interview.html, as available via the Internet and printed Dec. 11, 2013, 6 pages.
Echolocation allows blind to 'see' using sound, CTV News, May 2011, web page at www.ctvnews.ca/echolocation-allows-blind-to-see-using-sound-1.648370, as available via the Internet, 2 pages.
Echolocation makes mountain biking, skiing possible for the blind, Here and Now, Jun. 2011, web page at hereandnow.wbur.org/2011/06/09/blind-extreme-sports, as available via the Internet, 5 pages.
Echolocation: using your ears to help you 'see', VisionAware, Jun. 2013, web page at www.visionaware.org/blog.aspx?BlogID=9&BlogEntryID=769, as available via the Internet, 13 pages.
Meet Ellen Herlache, Saginaw Valley State University, web page at www.svsu.edu/discover/meetsvsuseries/ellenherlache, as available via the Internet and printed Dec. 11, 2013, 3 pages.
How human echolocation allows people to see without using their eyes, Surprising Science, Aug. 2013, web page at blogs.

(56) References Cited

OTHER PUBLICATIONS smithsonianmag.com/science/2013/08/how-human-echolocation-allows-people-to-see-without-using-their-eyes, as available via the Internet, 8 pages.
How I was blindfolded—then tried to 'see' like a bat, The Independent, Jun. 2011, web page at www.independent.co.uk/news/science/how-i-was-blindfolded-ndash-then-tried-to-see-like-a-bat-2292457.html, as available via the Internet, 5 pages.
Humans can develop bat-like echolocation, Health—US News and World Report, Jul. 2009, web page at health.usnews.com/health-news/family-health/articles/2009/07/08/humans-can-develop-bat-like-echolocation, as available via the Internet, 1 page.
I can hear a building over there: blind echolocation experts use 'visual' part of their brain to process the clicks and echoes, Science Daily, May 2011, web page at www.sciencedaily.com/releases/2011/05/110525181420.htm?utm_source=feedburner&utm_medium=feed&utm_campaign=Feed:+sciencedaily+(ScienceDaily:+L . . . , as available via the Internet, 3 pages.
National Geographic Weekend Radio, Episode 1203—Air Date: Jan. 15, 2012, Hour 2—Daniel Kish, web page at radio.nationalgeographic.com/radio/ng-weekend-archives/1203, as available via the Internet, 9 pages.
World Congress Agenda for 2005—Northeast Regional Seminar Presentations, Dan Kish presentation, web page at www.wayfinding.net/iibnNECneseminar.htm, as available via the Internet, 10 pages.
Report: Blind children in U.K. being taught to 'see' by clicking tongues, Fox News, Feb. 2008, web page at www.foxnews.com/story/2008/02/10/report-blind-children-in-uk-being-taught-to-see-by-clicking-tongues, as available via the Internet, 2 pages.
Echo vision: The man who sees with sound, New Scientist, Issue 2703, Apr. 2009, pp. 31-33.
Sensitive as a bat: navigating the world by echoes, Physics Central, web page at www.physicscentral.com/explore/action/navigatingworld.cfm, as available via the Internet and printed Dec. 11, 2013, 3 pages.
Spanish scientists develop echolocation in humans, Phys Org., Jun. 2009, web page at phys.org/news165568028.html, as available via the Internet, 11 pages.
Unpredicted enhancement, Pop Biotheics, Apr. 2009, web page at www.popbiotheics.com/2009/04/unpredicted-enhancement, as available via the Internet, 4 pages.
Echolocation in the spotlight, Visibility, Winter 2007/2008, 8 pages.
Interview—13 Questions: Daniel Kish, Ouch! It's a disability thing, Jul. 2008, web page at www.bbc.co.uk/ouch/interviews/13-questions-.shtml, as available via the Internet, 2 pages.
Bat school for the blind, Teensville, BBC, Nov. 2010, web page at http://www.bbc.co.uk/programmes/b00vzyfy, as available via the Internet, 25 min video.
Brian Bushway leading the blind, Mountain Bike Action Magazine, Apr. 2009, web page at brianbushway.com/MBA90.91.pdf, as available via the Internet, 2 pages.
Mountain biking with the blind, Hard Tales, Mountain Bike Action, Feb. 2011, web page at http://www.nxtbook.com/nxtbooks/hitorque/mba_201102/index.php?startid=14#/14, as available via the Internet, 2 pages.
Canes mean freedom, parts one and two, Insight—Supporting blind and partially sighted young people, Issues 28/29, 2010, 10 pages.
Flash Sonar: using echoes to help you get around, Insight—Supporting blind and partially sighted young people, Issue 14, Mar./Apr. 2008, 6 pages.
How active echolocation works, Insight—Supporting blind and partially sighted young people, Issue 17, Sep./Oct. 2008, 3 pages.
Flash forward, Insight—Supporting blind and partially sighted young people, Issue 25, Jan./Feb. 2010, 5 pages.
Workshop for visually challenged, Calcutta Mercy Hospital, Jun. 2008, web page at www.calcuttamercyhospital.org/events-news/workshop-for-visually-challenged, as available via the Internet (abstract).
Blind students use 'bat vision' to see, Calcutta Mercy Hospital, Jun. 2008, web page at www.calcuttamercyhospital.org/events-news/blind-students-use-bat-vision-to-see, as available via the Internet, 2 pages.
Academic Science and Research, World Access for the Blind, Copyright 2000-2013, web page at www.worldaccessfortheblind.org/node/459, as available via the Internet, 4 pages.
Applied and Popular Science, World Access for the Blind, Copyright 2000-2013, web page at www.worldaccessfortheblind.org/node/464, as available via the Internet, 3 pages.
Art, Health, and Nature, World Access for the Blind, Copyright 2000-2013, web page at www.worldaccessfortheblind.org/taxonomy/term/48, as available via the Internet, 4 pages.
Blind student group course, World Access for the Blind, Copyright 2000-2013, web page at www.worldaccessfortheblind.org/node/400, as available via the Internet, 2 pages.
Daniel Kish voted talk of the day at poptech, World Access for the Blind, web page at www.worldaccessfortheblind.org/node/473, as available via the Internet, 2 pages.
Family Seminars, World Access for the Blind, web page at www.worldaccessfortheblind.org/node/403, as available via the Internet, 1 page.
From the public, World Access for the Blind, web page at www.worldaccessfortheblind.org/node/452, as available via the Internet, 3 pages.
Hike for blind youth and adults—Mar. 19, 2011, World Access for the Blind, web page at www.worldaccessfortheblind.org/node/214, as available via the Internet, 1 page.
Honors and accolades, World Access for the Blind, web page at www.worldaccessfortheblind.org/node/466, as available via the Internet, 4 pages.
Instructional materials, World Access for the Blind, web page at www.worldaccessfortheblind.org/taxonomy/term/23, as available via the Internet, 3 pages.
Learning and living with flashsonar, World Access for the Blind, web page at www.worldaceessfortheblind.org/node/502, as available via the Internet, 1 page.
News coverage of the brain scan study that illustrates that out vision truly is sound, World Access for the Blind, web page at www.worldaccessfortheblind.org/node/294, as available via the Internet, 2 pages.
No limits challenge events, World Access for the Blind, web page at www.worldaccessfortheblind.org/node/407, as available via the Internet, 1 page.
Notable interviews and presentations, World Access for the Blind, web page at www.worldaccessfortheblind.org/node/443, as available via the Internet, 4 pages.
Our instructional approach in action, World Access for the Blind, web page at www.worldaceessfortheblind.org/node/465, as available via the Internet, 4 pages.
Partnerships and research, World Access for the Blind, web page at www.worldaccessfortheblind.org/taxonomy/term/9, as available via the Internet, 3 pages.
Penetrating perspectives and items of interest, World Access for the Blind, web page at www.worldaccessfortbeblind.org/node/370, as available via the Internet, 4 pages.
Professional development workshops, World Access for the Blind, web page at www.worldaccessfortheblind.org/node/399, as available via the Internet, 5 pages.
Professional presentations and seminar, World Access for the Blind, web page at www.worldaccessfortheblind.org/node/402, as available via the Internet, 7 pages.
Professional workshops and forums—learning a new way, World Access for the Blind, web page at www.worldaccessfortheblind.org/node/451, as available via the Internet, 3 pages.
Program development and relief efforts, World Access for the Blind, web page at www.worldaccessfortheblind.org/node/404, as available via the Internet, 1 page.
Public awareness workshops, World Access for the Blind, web page at www.worldaccessfortheblind.org/node/405, as available via the Internet, 2 pages.

(56) References Cited

OTHER PUBLICATIONS

Recreation and sensory enrichment clinics, World Access for the Blind, web page at www.worldaccessfortheblind.org/node/406, as available via the Internet, 4 pages.
Reports from students, families, and friends about learning to see, World Access for the Blind, web page at www.worldaccessfortheblind.org/node/449, as available via the Internet, 7 pages.
Resources, World Access for the Blind, web page at www.worldaccessfortheblind.org/node/374, as available via the Internet, 3 pages.
Science, research, and higher education, World Access for the Blind, web page at www.worldaccessfortheblind.org/node/410, as available via the Internet, 1 page.
Spanish scientist study the effectiveness of sonar signals in humans, World Access for the Blind, web page at www.worldaccessfortheblind.org/node/200, as available via the Internet, 1 page.
TEDx talks, World Access for the Blind, web page at www.worldaccessfortheblind.org/node/479, as available via the Internet, 2 pages.
World Access for the Blind in Chihuahua, World Access for the Blind, web page at www.worldaccessfortheblind.org/node/401, as available via the Internet, 1 page.
World Access for the Blind Milestones, World Access for the Blind, web page at www.worldaccessfortheblind.org/node/411, as available via the Internet, 2 pages.
World Access for the Blind News and Events, web page at http://63.247.129.161/~wafb2005/recent_events.htm, as available via the Internet and printed Aug. 17, 2006, 6 pages.
Ker, J., Blind faith: sightless mountain bikers are getting a feel for the sport, Mountain Bike Action, May 2001, web page at www.mbaction.com, as available via the Internet, pp. 52-63.

* cited by examiner

Block Diagram Schematic of an Echolocation Device

Schematic of Band Pass Preamplifier Circuitry

Schematic of a Power Amplifier Circuitry

Schematic of a Braille Cell Interface Circuitry

Schematic of Power Source Circuitry that is a Lithium-Ion Polymer Battery Charger Schematic of a High Voltage Supply Circuitry

ECHOLOCATION SYSTEMS AND METHODS

FIELD

The present invention relates generally to devices for assisting the visually impaired to navigate their environment. More specifically the invention relates to an echolocation apparatus that may be used by a sightless person and to a method for generating sounds of controllable, predictable amplitude and frequency that can facilitate the navigation of a sightless person in an environment without being obtrusive to others in the immediate vicinity.

BACKGROUND

Human echolocation is the ability of a person to sense objects in his or her surroundings by generating a sound wave and then detecting echoes off of those objects. This ability can be used by an unsighted person to maneuver within his or her environment. The sound waves can be generated, for example, by making a clicking noise with the mouth or by tapping a cane. This phenomenon is similar in principle to active sonar used by submarines or to echolocation used by certain species of animals, such as dolphins or bats.

By interpreting the sounds reflecting off nearby objects, a person trained in human echolocation can determine the approximate location, dimensions, and depth of objects and use this information to navigate his or her environment. In one widely publicized example reported by CBS television news and *People* magazine, an unsighted teenage boy used echolocation to steer around objects while walking, roller skating, and participating in other normal daily activities.

A drawback to human echolocation is that the generated sounds are of a comparatively low frequency and rate. Consequently the surroundings cannot be evaluated with the same detail as echolocating animals such as dolphins and bats, which use a higher frequency. Further, the generated sounds are not always of the same amplitude or frequency, and the echoes bouncing off nearby objects are thus more difficult to interpret. In addition, the tapping and clicking noises can be obtrusive to sighted persons in the vicinity.

Thus there is a need for an improved human echolocation system.

SUMMARY

Stated generally, the present invention pertains to methods and apparatuses that aid an unsighted or partially sighted person in maneuvering within his or her environment by generating sound waves that echo off nearby surrounding objects, thereby assisting the unsighted or partially sighted person in determining the location or size of the surrounding objects.

For example, one disclosed embodiment comprises a device for creating sounds to echo off objects in an environment such that an unsighted person can hear the echoes and use them to assist in navigation, comprising: a central processing unit; a first memory operatively associated with the central processing unit and having stored therein first data corresponding to a first sound for use in creating echoes suitable for use in a first environment; a second memory operatively associated with the central processing unit and having stored therein second data corresponding to a second sound for use in creating echoes suitable for use in a second environment that is larger than the first environment; a transducer operatively associated with the central processing unit for converting electrical energy into acoustic energy; and wherein the central processing unit recalls one of the first data and the second data and generates an electrical output signal to cause the transducer to emit a tone associated with the recalled one of the first data and the second data.

As another example, one disclosed embodiment comprises a method for creating sounds to echo off objects in an environment such that an unsighted person can hear the echoes and use them to assist in navigation, comprising: determining features of an environment; retrieving acoustic data from a memory, the acoustic data corresponding to a first sound for use in creating echoes suitable for use in the environment; generating a transducer signal based at least in part on the acoustic data; and transmitting the transducer signal to a transducer in order to convert the transducer signal into acoustic energy. In other embodiments, a computer readable medium comprises program code for causing a processor to perform such a method.

These illustrative embodiments are mentioned not to limit or define the invention, but rather to provide examples to aid understanding thereof. Illustrative embodiments are discussed in the Detailed Description, which provides further description of the invention. Advantages offered by various embodiments of this invention may be further understood by examining this specification.

Objects, features, and advantages of the present invention will become apparent upon reading the following specification, when taken in conjunction with the drawings and the appended claims.

DETAILED DESCRIPTION

Figure 1:
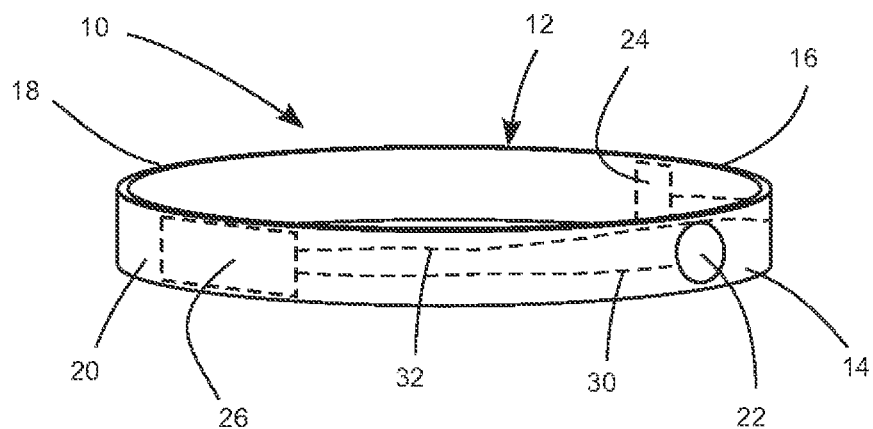
FIG. 1 is a perspective view of an echolocation device according to a disclosed embodiment.

The disclosed echolocation device may be used by an unsighted person and emits sounds that echo off nearby objects that can be sensed and analyzed by the user. In broad terms, the device generates a signal that will elicit a discernable echo that can be processed by a user. The actual tone generated by the speaker is thus less important than the quality of the echoes that the tone returns. There are a number of factors to consider when generating the tone to optimize the quality of the echo received by the user. And, as will be seen, the requirements for tones suitable for generating echoes off faraway objects differ from the requirements for tones for generating echoes off nearby objects.

Factors to be taken into account in generating a consistent tone include signal duration, frequency content, and/or amplitude shaping. A user can more quickly learn echolocation when variations in the signals are taken out of the equation.

Generating a consistent tone does not mean that the signal duration, frequency, and amplitude of every emitted signal must be the same. As will be discussed below, the signal duration, frequency, and amplitude of a signal emitted by the disclosed embodiment depend in large part upon the environment within which the user is operating. Whether the user is in a small, enclosed environment or a large, open environment will affect what duration, frequency, and amplitude is preferable. Other factors include whether the user is moving or stationary and the level of ambient noise in the environment. In this context, signals used for a particular type of environment should be consistent, understanding that a different environment may demand a signal of different duration, frequency, and amplitude.

The distance from the speaker to the targeted object is important for several reasons. All other things being equal, the further the distance from the speaker to the targeted object, the louder the signal must be. Because air absorbs high frequency sounds more than low frequency sounds, a low frequency tone is preferable to minimize the attenuation of the outgoing signal and returned echo. The use of lower frequency tones results in less attenuation as the sound travels through air, thus enabling a reduction in the volume of the emitted tones while still enabling the user to discern echoes from distant objects.

Further, at a longer distance there is a broader panorama of objects to reflect the tones, resulting in more echoes. The user requires longer to process the information. Also the length of time between the emission of the signal and the return of echoes from a distant object is longer than for a nearby object. So as not to emit a second signal before the first signal has returned, the delay between signals must be greater for distant objects. Thus the signals emitted by the disclosed embodiment are spaced apart by a time sufficient to provide the user the opportunity to process the more complex echo and to allow sufficient time for a first emitted signal to return to the user before a second signal is emitted.

Discriminating echoes from targeted objects that are closer to the user benefits from higher frequencies. Higher frequencies provide better spatial resolution for better discrimination. Higher pitched tones can be shorter in duration, more frequent, and, because they do not have to travel as far, quieter.

The echoes must necessarily be within the audible sound spectrum, or else the user would not be able to detect them. On the other hand, higher frequencies provide more accurate resolution. Consequently the echolocation device emits short, high pitched sounds in the audible spectrum that are heard as "chirps." In the disclosed embodiment, the sounds are 4 kHz and higher. Humans typically do not attend to sounds above 8 kHz, i.e., they can hear the sounds but typically ignore them unless they are specifically listening for them. Thus it is advantageous, but not essential, that the chirps be above 8 kHz and preferably above 10 kHz so as to be unobtrusive to sighted individuals in the vicinity.

A further step is optionally taken in the disclosed embodiment to minimize obtrusiveness of the chirps relates to the character of the sound. If the signal has few or no harmonics, the sound is pleasant to a human listener. But if harmonics occur at random or at uneven intervals, the sound is perceived as discordant. To ensure that the sound is not discordant, the disclosed embodiment emits either a sine wave or a square wave. There are no harmonics in a sine wave, and a square wave has few audible harmonics. Thus neither is perceived by a human listener as unpleasant.

In the disclosed embodiment, the chirps are emitted as downward sweeps over about an octave range. Downward sweeping allows the upper frequencies, which don't travel as far and which are more difficult for humans to hear, to reach the targets and return before lower frequencies, which travel farther and are easier to hear, and which therefore have the potential to mask higher frequencies. Sweeping over a range of frequencies makes possible richer information with signals containing many frequencies, because different frequencies offer different advantages.

The foregoing characteristics of the emitted chirp of the disclosed embodiment are not essential to the invention except as may be set forth in the claims below. For example, unless recited in the claims, the chirps are not limited to sine waves or square waves; the emitted frequencies may be other than those identified above; and the chirps can be upward sweeping or single frequency instead of downward sweeping and may range over more or less than an octave. As another example, composite pulses may be emitted.

Some of the disclosed embodiments optionally provide for signal sequencing. Signal sequencing provides users with the ability to create and playback sequences of different types of echo signals. Such sequences can be tailored to different types of activity of the unsighted user (e.g. whether the user is moving or stationary) and the particular environment (e.g. indoor, outdoor, street) in which these activities occur. The user can create sequences from different types of signals each individually tailored to detect different types of objects, for example, nearby objects versus more distant objects. In addition the user has control over the repetition rates for each signal, and the alternation patterns between the signals.

By taking some or all the foregoing factors into account, the disclosed echolocation device can generate tones that produce a discernable echo that can be processed by a user.

Figure 2:
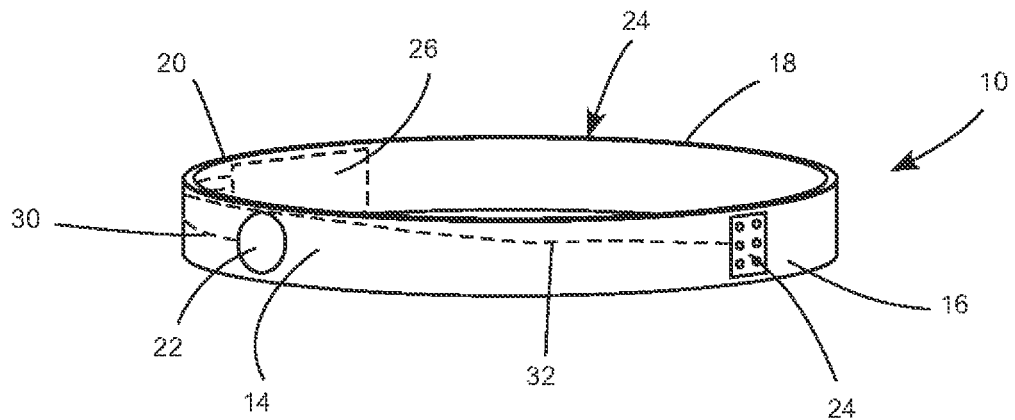
FIG. 2 is a rotated view of the echolocation device of FIG. 1.

Referring now to the drawings, in which like numerals indicate like elements throughout the several views, FIGS. 1 and 2 depict an embodiment of an echolocation device 10. The device 10 includes a band 12 with front 14, left 16, back 18, and right 20 sides. The band 12 is intended to fit securely around the head of a user. A piezoelectric speaker 22 is located at the front 14 of the band 12 to emit sounds whose echoes are sensed by the user. A Braille cell interface 24 by which the user can enter commands is mounted on the left side 16 of the band 12. A board 26 containing circuitry of the echolocation device 10 is mounted on the right side 20 of the band.

An electrical path 30 inside the band 12 connects the board 26 to the speaker 22. An electrical path 32 inside the band 12 connects the board 26 to the Braille cell interface 24.

The band 12 preferably fits securely around the head of the user much like an athletic headband. The secure fit can be accomplished in any number of ways. The band 12 can be made of a substantially non-extensible material, and the user selects the size band that fits him or her in much the same way that one selects a hat size. Or the material of the band 12 can be somewhat elastic so that it stretches over the user's head and then returns toward its normal shape to securely fit the user's head.

Alternate arrangements, well known in the field of baseball and golf caps, can be used to provide an adjustable, secure fit for the band 12. In each of these arrangements the band 12 is split in the back 18, and the two ends of the band 12 are then connected by one of the following arrangements.

In one embodiment a connector includes a first strap with a plurality of holes, which partially overlaps a second strap with a plurality of pins. Each of the pins is shaped and sized to form an interference fit with a corresponding hole. By adjusting the overlap of the two straps, and how many pins engage the holes, the length of the connector, and hence the length of the band 12, can be adjusted to provide a comfortable fit.

In another embodiment a connector includes overlapping straps. The straps have strips of interlocking hook and loop fabric, e.g., Velcro, on mutually facing portions. By adjusting the overlap of the two straps and securing the straps with the strips of interlocking hook and loop fabric, the length of the connector, and hence the length of the band 12, can be adjusted to provide a comfortable fit.

In still another embodiment a connector includes a first strap with a buckle mounted to its end. A second strap has a plurality of holes spaced along its length. A tongue is pivotably mounted to the buckle. The tip of the second strap is inserted into the buckle. By adjusting the overlap of the two straps and inserting the tongue of the buckle through a corresponding hole in the second strap, the length of the connector, and hence the length of the band 12, can be adjusted to provide a comfortable fit.

In yet another embodiment, a connector includes first and second straps. The first strap has a buckle mounted to its end. Unlike the connector described in the preceding paragraph, this connector has no tongue on the buckle, and the second strap has no holes. Instead, when the second strap is inserted through the buckle, friction between the strap and the buckle maintains the straps at the desired overlap. By adjusting the overlap of the two straps, the length of the connector, and hence the length of the band 12, can be adjusted to provide a comfortable fit.

The connectors described above are only a few ways of providing adjustability to the length of the band 12 and are presented only for purposes of illustration.

It is not essential that the echolocation device be mounted to a headband. Mounting the device on a headband provides perhaps a more natural experience, as it is human nature to turn one's head in the direction of the area of the environment they want to process. By locating the speaker on the user's forehead, the emitted sound is sent out in the direction the user is facing. Mounting the device on a baseball-type cap or the like would also provide these advantages. But the invention also contemplates mounting the speaker on a chain worn as a necklace, or a clip- or pin-arrangement by which the speaker can be temporarily attached to the user's clothing. In other embodiments, a speaker may be mounted on any number of surfaces or objects, including but not limited to, a visor, glasses, cane, or handheld device.

There is also no requirement that the Braille cell interface 24 be mounted to the same article as the speaker and electronics. The Braille cell interface can be equipped with Bluetooth® or other suitable wireless communications protocol and carried, for example, in the user's pocket. When the user needs to access the user interface, he simply reaches into his pocket and manipulates the Braille cell interface, and the control signal is sent wirelessly to the electronics. This arrangement has the advantage of being operable more discretely than a user interface mounted to a cap or headband. In another embodiment, the Braille cell interface is mounted on another object such as a cane.

Block Diagram Schematic

Figure 3:
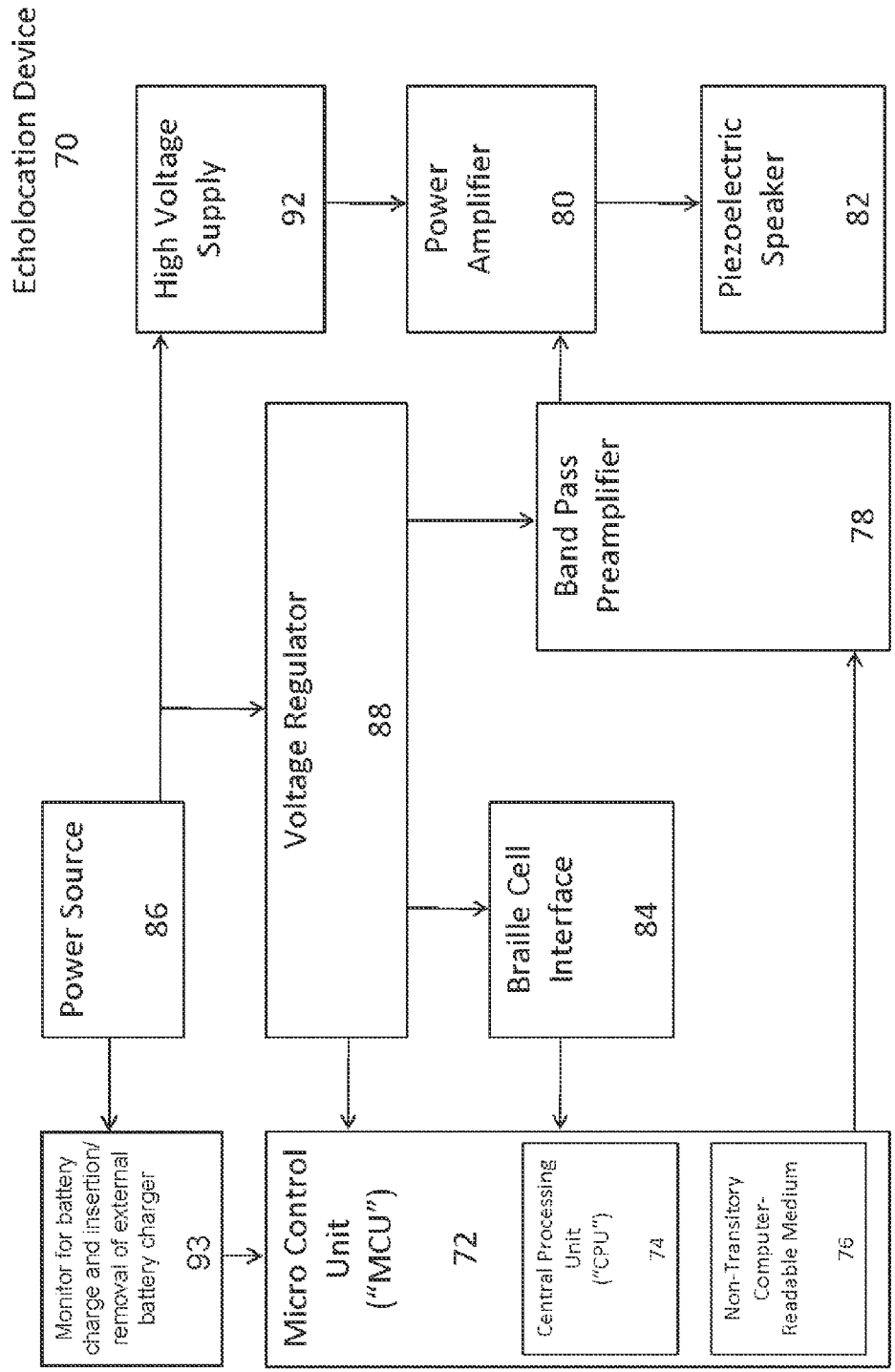
FIG. 3 is a block diagram schematic of an echolocation device according to one embodiment of the present invention.

FIG. 3 is a block diagram schematic showing various components of an echolocation device 70 according to one embodiment of the present invention. The echolocation device 70 disclosed in FIG. 3 includes a micro control unit ("MCU") 72, a band pass preamplifier 78, a power amplifier 80, a piezoelectric speaker 82, a Braille cell interface 84, a power source 86, a voltage regulator 88, and a high voltage supply 92. Electronics 93 in line from the power source 86 to the MCU 72 monitors remaining battery charge and the insertion/removal of the external (wall) charger for the battery.

A user interacts with the echolocation device 70 through the Braille cell interface 84 and through audible feedback from the piezoelectric speaker 82. By depressing a button, or buttons in a combination, that corresponds to Braille characters on the Braille cell interface 84, the user can control the operation of the echolocation device 70. Software code can be executed by the MCU 72 to cause the MCU 72 to control the echolocation device 70 based upon the button or button combination received via user inputs into the Braille cell interface 84. The voltage regulator 88 can provide power to the MCU 72. The power source 86 can provide power to the various components from an external power source or from stored power.

The MCU 72 can also generate a chirp waveform. The band pass preamplifier 78 receives the chirp waveform generated by the MCU 72 and can include low pass filters, high pass filters, or both that may provide anti-aliasing of the generated chirp waveform and may help compensate for any decreased sensitivity in both the piezoelectric speaker 82 and human hearing at higher frequencies. The power amplifier 80 drives the piezoelectric speaker 82. The piezoelectric speaker 82 outputs the sound of the chirps generated by the MCU 72. The high voltage supply 92 provides energy to the power amplifier 80 that drives the piezoelectric speaker 82.

Micro Control Unit ("MCU")

The embodiment of the echolocation device 70 shown in FIG. 3 includes an MCU 72. An MCU 72 according to some embodiments includes a central processing unit ("CPU") 74 and a non-transitory computer-readable medium 76, such as read-only memory, random access memory, or both. The CPU 74 can execute software code that may cause the MCU 72 to control the echolocation device 70. In various embodiments, the software code may be programmed in particular languages. For example, in various embodiments, assembly language, C, C++, BASIC, or any other suitable software language may be used. The non-transitory computer-readable medium 76 can store executable code that, when executed by the CPU 74, can cause the MCU 72 to control the echolocation device 70. For example, the MCU 72 may generate a chirp waveform that is outputted by the piezoelectric speaker 82. In various embodiments, the non-transitory computer-readable medium 76 may include EPROM, EEPROM, RAM, ROM, or any other suitable computer-readable medium.

In an embodiment, the MCU 72 is from the Microchip "PIC 18" family. In another embodiment, the MCU 72 is from the "PIC 17" family. In various embodiments, the MCU 72 may be any other suitable micro control unit. For example, the MCU 72 may be a Freescale 68HC11, STMicroelectronics STM8, Rabbit 2000, Toshiba TLCS-870, or Zilog ez80. In some embodiments, an 8-bit, 16-bit, 32-bit or other x-bit MCU 72 may be used.

In some embodiments, the MCU 72 comprises at least one processor. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices. The processor may comprise code for carrying out one or more of the methods (or parts of methods) described herein.

The MCU 72 can interact with the user through the Braille cell interface 84 and through audible feedback, such as audible feedback tone sequences, provided by the piezoelectric speaker 82. The echo signal may be generated using pulse width modulation ("PWM") or a similar modulation technique. In one embodiment, a PWM module is included within the MCU 72. In other embodiments, a PWM module is implemented by hardware external to the MCU 72. Still in other embodiments, the waveforms for an echo signal are generated using other forms of modulation such as pulse-code modulation ("PCM"). In one embodiment, a user can adjust the audible feedback provided by a speaker by adjusting controls on the Braille cell interface. For example, the user may adjustment the audible feedback such that the quality of the echoes off surrounding objects becomes clearer.

The waveforms for an echo signal can be generated in real-time. In one embodiment, all or part the data of the waveform is stored in a non-transitory computer-readable medium 76. Certain embodiments of MCU 72 can include sufficient memory to store data for a 16 ms waveform. The generated waveform of the chirp can be provided to a band pass preamplifier 78. The resulting signal is then provided to a power amplifier 80 that drives a piezoelectric speaker 82.

Band Pass Preamplifier

To optimize the signal to produce a discernable echo, the signal is preferably limited to a narrow bandwidth. However, the signal generated by the MCU contains frequencies both above and below the desired frequency. In particular, frequencies higher than the desired frequency contain aliasing signals.

Furthermore, the digital output of the MCU must be converted into an analog signal before it reaches the speaker.

To eliminate aliasing and voltage transients from the signal generated by the MCU and to convert the digital signal from the MCU into an analog signal, the MCU output is run through a band-pass preamplifier 78. The band-pass preamplifier 78 comprises a plurality of band-pass filters. "High pass" filters allow frequencies of the signal higher than the desired frequency to pass but attenuate the frequencies below the desired frequency. "Low pass" filters allow frequencies of the signal lower than the desired frequency to pass but attenuate the frequencies above the desired frequency.

Band pass filters are typically described as having a cutoff frequency. On one side of this frequency the signals pass through unimpeded. On the other side they are attenuated. Frequencies close to the cutoff frequency, but still on the attenuating side, will have their amplitude reduced less than frequencies further from the cutoff frequency. In an example, a low-pass filter has a cutoff frequency of 1 kHz, and the filter supports an attenuation of 6 dB per octave. A pure sine wave with a frequency of 2 kHz will have its amplitude attenuated by 6 dB, and a 4 kHz wave, which has a frequency further from the cutoff frequency, will have its amplitude reduced by 12 dB. A frequency of 1.1 kHz (close to the cut off frequency) will hardly be attenuated at all. This example is typical for a single pole, passive resistor-capacitor (RC) filter.

If a greater attenuation than 6 dB per octave is needed, two RC filters with the same cutoff frequency could be connected together in series. The two RC filters in series would comprise a two-pole passive filter and have an attenuation of 12 dB per octave. In theory a large number of such filters could be strung together in this way to make the cutoff as sharp as needed. However, in practice simple filters like this interact with each other so that two adverse consequences occur. First, the attenuation gets less with each stage. And second, the frequencies close to the cutoff frequency on the "pass" side begin to experience some attenuation as well.

To address this and other disadvantages, the disclosed embodiment employs one passive low-pass filter 94 in series with an active low-pass filter 98. The low-pass filter 94 is a two-pole RC filter circuit having an attenuation of 12 dB per octave. The cutoff frequency is around 30 kHz to make sure the useful part of the signal is not degraded. The primary function of the first low-pass filter 94 is to attenuate some large, very high frequency voltage transients coming from the MCU. These transients have 'high power' contributions that are in the MHz range. In theory, the first low-pass filter 94 could be eliminated, and the transients could be attenuated by the active low-pass filter 98. But filtering out these very high frequencies early on is easy to do with simple circuitry, costs practically nothing, and reduces some of the technical demands on the active low-pass filter 98.

In such an embodiment, the major portion of high-frequency attenuation is accomplished by the active low-pass filter 98, which comprises a Chebyshev circuit well known to those skilled in the art. The output of the MCU used in the disclosed embodiment has a large frequency component near 80 kHz, just 2 octaves from the highest frequency content of the signal. By combining active (powered) and passive components, the active low-pass filter 98 can create a very rapid attenuation of frequencies near the cutoff frequency. In one example, a two stage, four pole design attenuates in the stop band of more than 24 dB per octave.

High-pass filter 96 is a voltage shifter. The average voltage of the signal that enters the low-pass filter 98 needs to be at a point which is approximately halfway between the maximum output voltage of low-pass filter 98 and ground (0 volts) of the input amplifiers. The high-pass filter 96 modifies just enough of the DC bias voltage (or DC offset) to achieve this result. To some extent the signal voltage can be tuned by adjusting the output of the MCU. The high-pass filter 96 shifts the voltage of the adjusted output of the MCU to achieve the voltage required by the low-pass filter 98 and compensates for any shifting caused by the low-pass filter 94 and other circuits in the area.

The high-pass filter 100, on the other side of the low-pass filter 98, serves much the same purpose as the high-pass filter 96. It is a level-shifting circuit designed to center the output of the low-pass filter 98 on the input terminals of the power amplifier.

In operation the band pass preamplifier 78 receives a chirp waveform generated by the MCU 72, filters the waveform using the low-pass filters 94, 98 and the high-pass filters 96, 100. The band-pass preamplifier outputs the waveform to a power amplifier 80. The low-pass filters 94, 98 provide any needed anti-aliasing of the generated chirp waveform. The high-pass filters 96, 100 may assist in compensating for decreased sensitivity in both the piezoelectric speaker 82 or human hearing at higher frequencies. In some embodiments, the generated waveform has a sampling frequency of approximately 80 kHz.

It will be appreciated that the Chebyshev design is not the only suitable active low-pass filter 98. Other filter circuits also combine active and passive elements to achieve similar filtering results. Each has its advantages and disadvantages in terms of cost, complexity, and the effects of frequencies in the pass band near the cutoff frequency.

Figure 4:
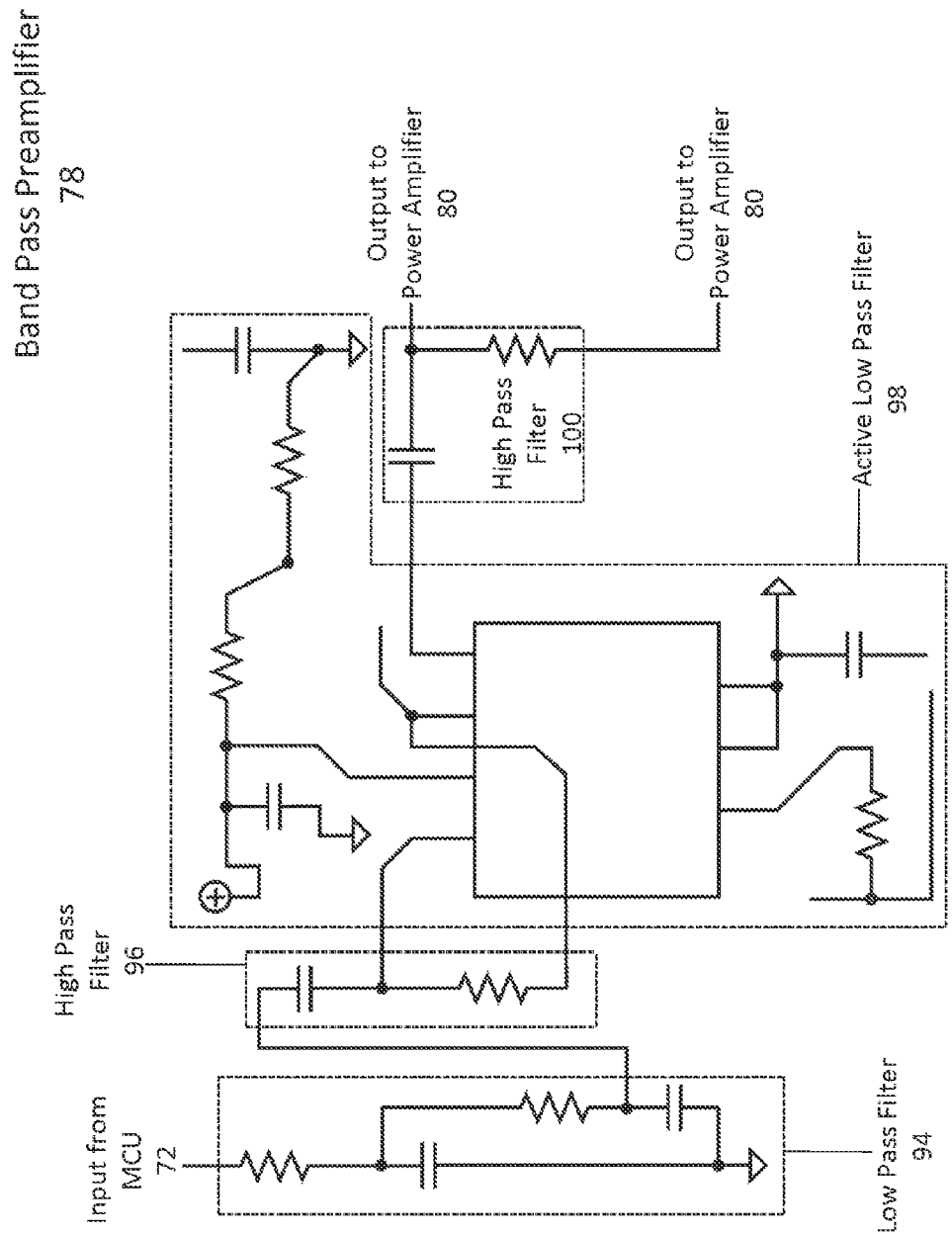
FIG. 4 is a schematic of band pass preamplifier circuitry according to one embodiment of the present invention.

In the embodiment disclosed in FIG. 4, the low-pass filters 94, 98 of the band-pass preamplifier 78 are implemented with a switched capacitor network that simulates a four pole (25 db/octave) Chebyshev filter. In addition, the passive high-pass filters 96, 100 shown in FIG. 4 are implemented with two RC voltage dividers, with one being placed before the active low-pass filter 98 and a second being placed immediately before the input stage of the power amplifier 80. In one embodiment, the MCU 72 performs additional shaping of the waveform during computation of the waveform. In other embodiments, hardware performs additional shaping of the waveform, which may increase the dynamic range of the echolocation device 70.

Power Amplifier

Power amplifier 80 may be any type of device, collection of devices, or circuitry that is suitable to drive a piezoelectric speaker 82. In one embodiment of the present invention, the power amplifier 80 drives both terminals of the piezoelectric speaker 82 with a 180° phase shift. That is, one terminal of the piezoelectric speaker can be pulled high while the other terminal can be pulled low, and vice versa. When operated in this configuration, the AC voltage swing measured at the terminals of the piezoelectric speaker 82 is twice the DC voltage produced by the high voltage supply 92.

Figure 5:
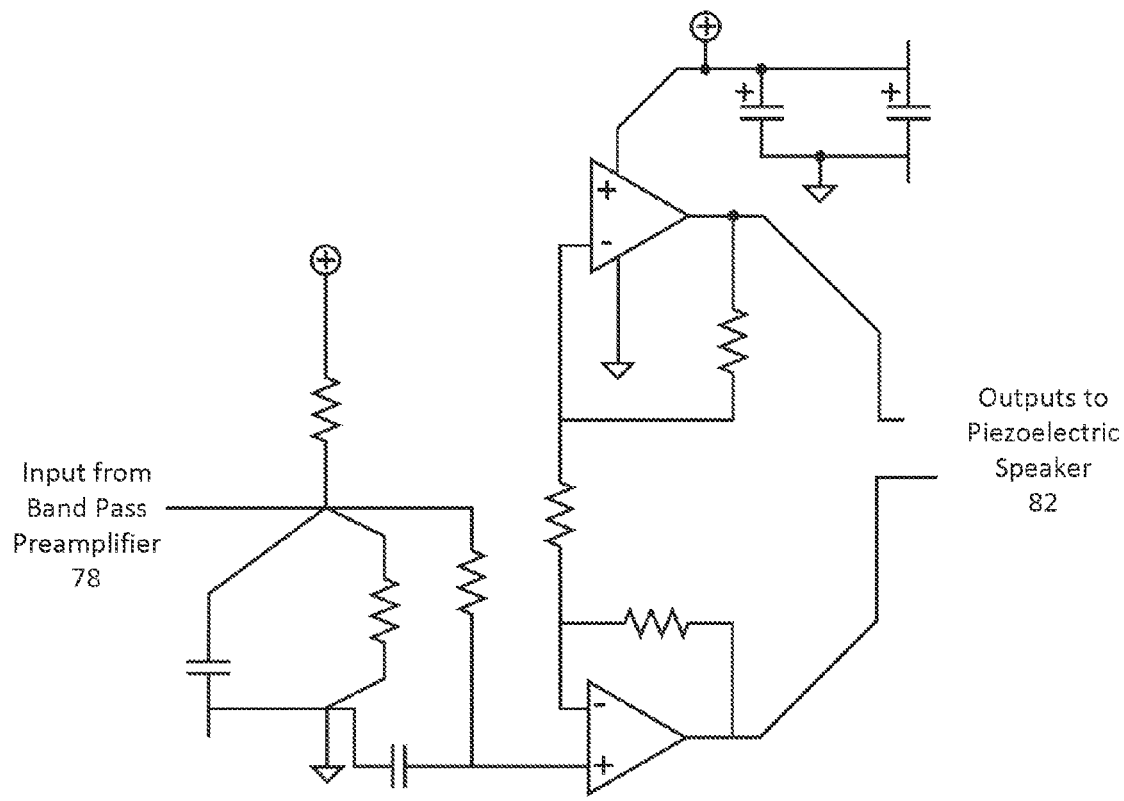
FIG. 5 is a schematic of power amplifier circuitry according to one embodiment of the present invention.

FIG. 5 discloses a circuit schematic of a power amplifier 80 that drives a piezoelectric speaker 82 according to one embodiment. The embodiment shown in FIG. 5 is a surface mount technology ("SMT") power amplifier 86, which drives both terminals of the piezoelectric speaker 82. According to the embodiment shown in FIG. 5, the power amplifier 80 receives a generated waveform from the band pass preamplifier 78 and outputs the waveform to a piezoelectric speaker 82.

Piezoelectric Speaker

The speaker 82 may be any type of device, collection of devices, or circuitry that can provide suitable output for the echolocation device 70. In one embodiment, any suitable piezoelectric speaker 82 may be used. As FIG. 3 illustrates, the echolocation device 70 incorporates a piezoelectric speaker 82 to output the sound of the chirps generated by the MCU 72. The power amplifier 80 powers the piezoelectric speaker 82. The piezoelectric speaker 82 receives the generated waveform from the power amplifier 80. According to one embodiment of the present invention, the piezoelectric speaker 82 is a ceramic-based speaker. For example, the piezoelectric speaker 82 may be a Motorola KNS-1005. Because the frequency response of such speakers is not ideal, some embodiments of the present invention incorporate a tuned piezoelectric speaker 82 that can provide sensitivity at critical frequencies. For example, the piezoelectric speaker 82 may have a sharp (10+ db per octave) resonance at 18-20 kHz with a sensitivity of approximately 12 dB at resonance. One advantage of using such a piezoelectric speaker 82 is that the increased sensitivities reduce the required output, which may increase the battery life for the echolocation device 70.

User Interface

The user interface 84 may be any type of device, collection of devices, or circuitry that can receive input from a user and provide a signal that is input to the MCU 72 of the echolocation device 70. In one embodiment of the present invention, a Braille cell interface is used. A Braille cell interface provides a compact, flexible, user interface that is optimized for use by unsighted people by basing it on the configuration of the Braille cell, and by implementing user entry codes through button combinations that are consistent with Braille letter configurations. The Braille cell interface can be of either the six dot (ASCII) or eight dot (Unicode) variety.

The outputs of the Braille cell interface 84 are voltage levels corresponding to the associated dot key that is depressed. For example if dot key 1 is depressed, the corresponding voltage output by the Braille cell interface 84 associated with dot key 1 may be below a minimum threshold voltage such that the MCU 72 is able to ascertain that dot key 1 is depressed.

Figure 6:
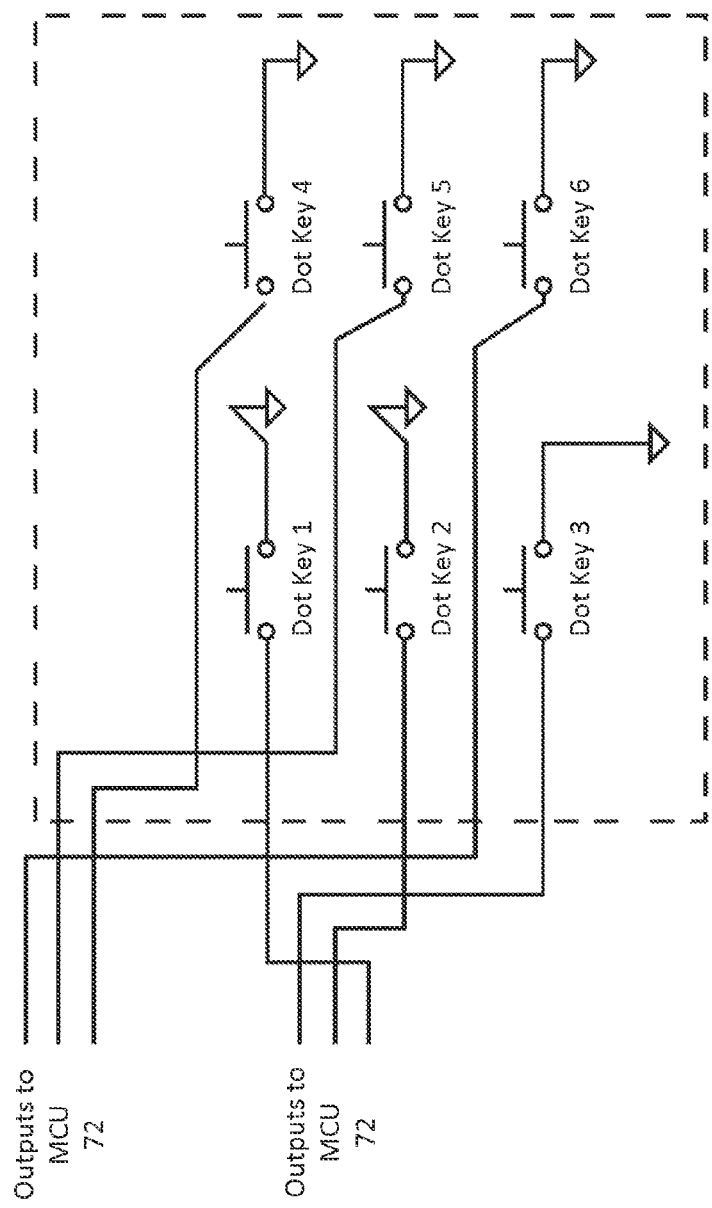
FIG. 6 is a schematic of Braille cell interface circuitry according to one embodiment of the present invention.

FIG. 6 depicts one embodiment of a circuit schematic of a Braille cell interface 84. In the embodiment shown in FIG. 6, the Braille cell interface 84 includes six buttons or "dot keys" that are positioned in the shape of a standard Braille cell. In one embodiment, dot 1 of the cell is distinguished by a different shape than the remaining dot keys. By depressing a button or buttons in a combination that corresponds to Braille characters on the Braille cell interface 80, the user can control the operation of the echolocation device 70. In an embodiment, the Braille cell keypad provides tactile feedback for at least 100,000 activations before needing to be replaced. In one embodiment of the present invention, each control function is assigned to a different Braille symbol representing a command code for the device. According to one embodiment, if the command code is more than one dot, the dots can be depressed in any order. In another embodiment, if the command code is more than one dot, the dots are depressed simultaneously. In one embodiment, the command code starts when the first dot key is depressed and ends when all dot-keys have been released.

For example, the command code "X" requires that the dot keys 1, 3, 4, and 6 be depressed. In various embodiments of the present invention, the keys may be depressed in different sequences or at different times. Thus, according to one embodiment of the present invention, the user may depress and hold dot 3 while using another finger to depress and release dots 1, 4, and 6 in any order or simultaneously, and then the user releases dot 3. In another embodiment, the user may depress and hold dot 1 while sequentially depressing dots 3, 4, and 6 in any order. In some embodiments, the user may depress and hold two or more of the required dot-keys simultaneously while depressing the remaining dot-keys in any order or simultaneously. In other embodiments, the user may depress one or more of the dot-keys before the required combination has been completed as long as at least one dot-key remains depressed until the combination has been completed. For example, using the dot keys for command code "X" as described above, the user may depress and hold dot key 1, then depress and hold dot key 3, then release dot key 1, then depress and hold dot key 4, then release dot key 3, then depress dot key 6 after which command code "X" will be activated. In another embodiment, dot keys 1, 3, 4, and 6 may be simultaneously depressed and released in any order or simultaneously.

Other types of user interfaces can also be used. The device can be outfitted with a small microphone that interfaces with the processor for voice recognition of commands from the user. Or the user interface can comprise one or more dials, sliders, push buttons, rocker switches, or the like. In one embodiment, the user interface comprises a button or other input device that a user can press to manually trigger a tone. For example, in an embodiment, when a user presses this button, the echolocation device outputs a sound having a predetermined frequency of between 6 and 8 kHz. In other embodiments, any suitable frequency and/or frequencies may be output when a user interacts with the echolocation device in a particular manner such as pressing one or more particular buttons, pressing and holding one or more particular buttons, and/or depressing one or more particular buttons.

Power Source, Battery Charger, Voltage Regulator, and High Voltage Supply

Power source 86 may be any type of device, collection of devices, or circuitry that can provide suitable power for a desired length of time to various other components of the echolocation device 70. In one embodiment of the present invention, the power source 86 may be any conventional rechargeable battery or batteries. The power source 86 may also be any non-rechargeable battery, such as alkaline battery or batteries. In addition, the power source 86 may be any other suitable voltage source, such as a conventional outlet plug or solar panel. Furthermore, in one embodiment of the preset invention, two or more batteries are in parallel. In another embodiment, two or more batteries are in series.

In one embodiment, the power source 86 includes two rechargeable lithium-ion polymer batteries having a nominal voltage of approximately 7.4 Volts. The two lithium-ion polymer batteries may be in parallel to provide greater longevity before requiring recharging. In various embodiments of the present invention, the nominal voltage of the power source 86 may be greater than or less than 7.4 Volts.

According to some embodiments, the lithium-ion polymer batteries arrangement starting at full charge can allow the echolocation device 70 to generate at least 30,000 chirps at approximately 94 dB prior to requiring recharging. In some embodiments, the echolocation device 70 may generate more or less than 30,000 chirps before requiring recharging.

In one embodiment, the lithium-ion polymer batteries arrangement can allow the echolocation device 70 to be stored in "off mode," as discussed below, for at least thirty days without requiring recharging. Moreover, in some embodiments, the power source 86 may allow the echolocation device 70 to operate the device in "indoor mode" or "outdoor mode" for at least seven hours before requiring recharging. Furthermore, in various embodiments, the power source 86 may operate the device for more or less than seven hours before requiring recharging.

In some embodiments, the current draw for powering the echolocation device 70 may result in the battery or batteries not fully discharging before becoming unusable to generate chirps. In one embodiment, one or more capacitors are used to store energy thereby reducing this inefficiency.

Figure 7:
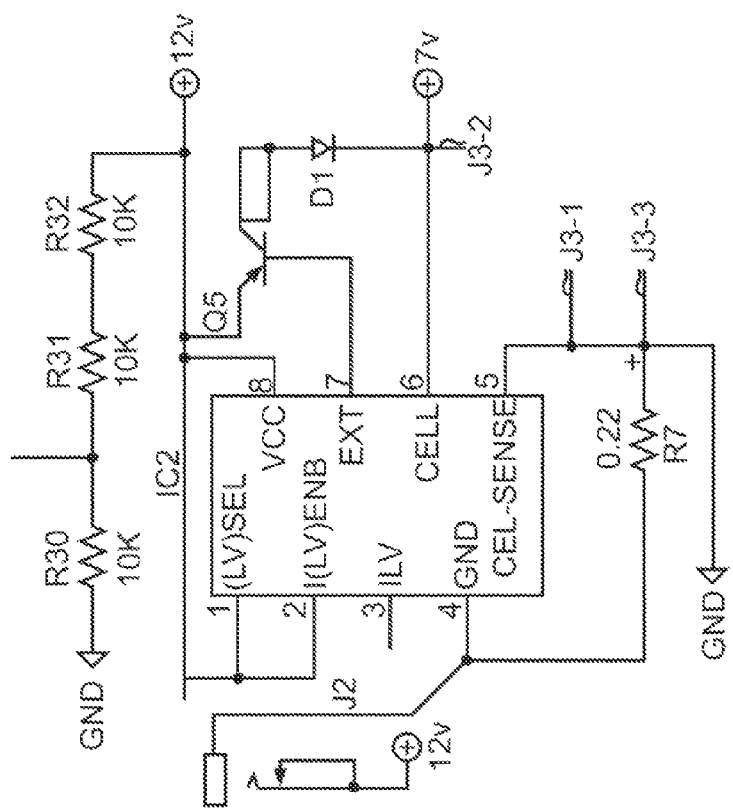
FIG. 7 is a schematic of power source circuitry that is a lithium-ion polymer battery charger according to one embodiment of the present invention.

A power source 86 according to some embodiments can include battery charger for recharging batteries. FIG. 7 provides a schematic of battery charger circuitry 90 that is a lithium-ion polymer battery charger according to one embodiment. The battery charger circuitry 90 can be disposed in, or associated with, power source 86 in FIG. 3. In an embodiment, one or more rechargeable batteries may be recharged using a 12 Volt DC power supply. Furthermore, in an embodiment, the battery charger circuitry 90 provides charging signals of the Constant Current, Constant Voltage ("CCCV") type to one or more batteries. In some embodiments, the voltage of the power supply may be more or less than 12 Volts. In other embodiments, one or more rechargeable batteries may be charged using non-CCCV signals such as by using a Phase-Locked Loop ("PLL") to track the resonance of the batteries as charging progresses. In another embodiment, the MCU 72 monitors battery charge and discharge thereby reducing or eliminating the need for the battery charger 90.

The embodiment shown in FIG. 3 depicts a voltage regulator 88. The voltage regulator 88 may be any type of device, collection of devices, or circuitry that can provide suitable voltage regulation to various other components of the echolocation device 70. In one embodiment, the voltage regulator 88 is a transistor-transistor logic ("TTL") supply. In an embodiment, the voltage regulator 88 has a nominal voltage of approximately 5 Volts. In various embodiments, the voltage regulator 88 may be a supply other than a TTL supply. In addition, the nominal voltage of the voltage regulator 88 may be more or less than 5 Volts according to various embodiments of the present invention. The voltage regulator 88 provides power to the MCU 72.

Figure 8:
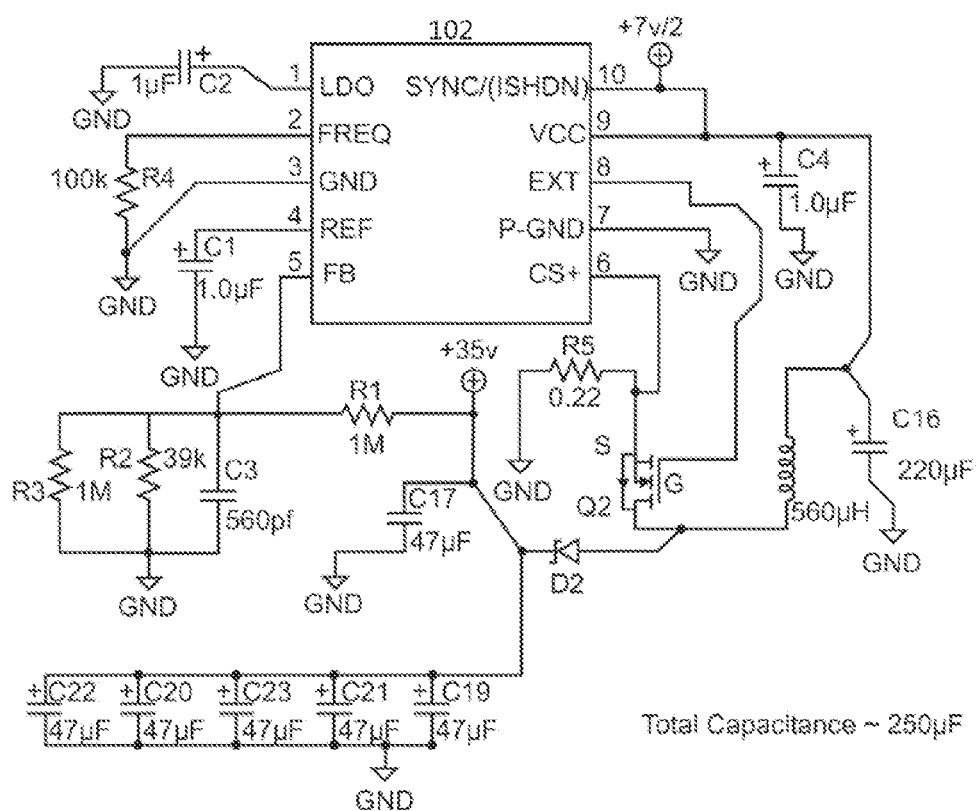
FIG. 8 is a schematic of high voltage supply circuitry according to one embodiment of the present invention.

The high voltage supply 92 shown in FIG. 3 provides energy to the power amplifier 80 which drives the piezoelectric speaker 82. FIG. 8 schematically depicts circuitry for high voltage supply 92 according to one embodiment of the present invention. The high voltage supply 92 depicted in FIG. 8 is a DC-DC converter, which incorporates a microchip 102 made by Maxium, the Max668/Max669. While these chips by Maxium have a preferred voltage of less than 28 Volts, there is no practical limitation to the voltage generated by these devices. For example, at least up to 90 Volts can be generated using a Maxium Max669 chip. In an embodiment of the present invention, the voltage generated by the high voltage supply 92 is less than 100 Volts. For example, in an embodiment, the nominal voltage of the high voltage supply 92 is 30 Volts. Any suitable high voltage supply 92, however, may be used.

According to one embodiment of the present invention, the high voltage supply 92 or one or more chips used in the high voltage supply 92 may operate in a low power "idle" mode where there is no load thereby potentially extending the amount of time that the echolocation device 70 can operate without needing to be recharged. Furthermore, according to one embodiment of the present invention, the high voltage supply 92 may be controlled by the MCU 72.

Operating Modes

The following operating modes of the disclosed embodiments are for illustrative purposes. Aspects and embodiments of the present invention include variations on these illustrative operating modes.

The echolocation device 70 of the disclosed embodiment includes four operating modes—two navigation modes and two inactive modes. The two navigation modes can include "outdoor mode" and "indoor mode." The two inactive modes can include "mute mode" and "off mode." Each mode of operation can have two different chirps, which are designated "A" and "B" for purposes of discussion. These chirp definitions can be altered and, if necessary, returned to the default by the user. In an embodiment of the present invention, the chirp definitions are defined in the software running on the MCU 72.

Outside mode can be used for exterior or large interior environments where there are few echo reflection surfaces. In one embodiment, the default chirps of outside mode are louder than those of the indoor mode. According to one embodiment, the default chirps of outside mode are at lower frequencies than the default chirps of inside mode, which allows the echo signal to travel further and to be heard at lower volumes as compared with inside mode, even though the lower frequencies may reduce discrimination slightly. For example, according to one embodiment, the chirps of the echolocation device 70 in outdoor mode may have a frequency of between 6 and 12 kHz, whereas the chirps in indoor mode may have a frequency of between 10 kHz and 20 kHz. Thus, in embodiments, aspects such as frequency, duration, etc., of one or more sounds output by the echolocation device depends upon the mode in which the device is operating. The amplitude of the chirps is not easily expressed numerically, because the actual tone generated by the speaker is less important than the quality of the echoes that the tone returns. By way of example only, and without limiting the scope of the invention, the amplitude of the chirps in indoor mode may be approximately 80% of the amplitude of the chirps in outdoor mode.

In one embodiment, when in outside mode, the two chirps are automatically triggered in the sequence "A," "A," "B," and the user may be unable to change the chirp sequence. In another embodiment, the chirp sequence may be altered and set by the user. In some embodiments, the chirp rate is user controlled. Still other embodiments allow the user to trigger manually a chirp of type A or type B at any time. In other embodiments, any number of patterns may be used in one or more sequences. For example, in one embodiment, an "A," "A," "B," "A" pattern is used. In another embodiment, an "A," "B," "A," "B" sequence is used. In embodiments, one of the two chirps (e.g., A or B) corresponds with short range sensing and the other chip corresponds with long range sensing. For example, in one embodiment, chirp A is for short range sensing and is configured for a set of frequencies between 9 and 18 kHz. In this embodiment, chirp B is for long range sensing and is configured for a set of frequencies between 7 and 14 kHz. In some embodiments, one or more chirps output for long range sensing is output less frequently than one or more chirps for short range sensing. In other embodiments, one or more chirps output for long range sensing is output more frequently than one or more chirps for short range sensing. Numerous other embodiments are disclosed herein and variations are within the scope of this disclosure.

In embodiments, one or more environments may each be associated with a chirp sequence. For example, in one embodiment, a first environment (such as an indoor environment) corresponds with a first chirp and a second chirp. In this embodiment, the first chirp and the second chirp may alternate in an first, second, first, second pattern. In an embodiment, a second environment (such as an outdoor environment) corresponds with a third chirp and a fourth chirp. In one embodiment, the third chirp and the fourth chirp alternate in a third, fourth, third, fourth pattern. In another embodiment, the third chirp and the fourth chirp alternate in a third, third, third, fourth pattern. In embodiments, a first range of frequencies corresponding to the first and second chirps of the first environment may be higher than a second range of frequencies corresponding to the third tone and fourth tone of the second environment. Numerous other embodiments are disclosed herein and variations are within the scope of this disclosure.

The default chirp definitions of inside mode are designed for most indoor activities. The chirps are quieter and higher in frequency as compared to chirps in outside mode, providing superior discrimination of smaller, closer objects. In one embodiment of the present invention, when in inside mode, only chirp "A" is automatically outputted. In other embodiments, chirp "A" and chirp "B" are outputted in one or more sequences. In one embodiment, the chirp rate is user controlled. Still other embodiments allow the user to trigger a chirp of type A or type B manually at any time.

In mute mode, a short, quiet tone sounds periodically. For example, in one embodiment of the present invention the tone sounds approximately every thirty seconds. The intent of the tone is to remind the user that the echolocation device is still on and consuming power. In one embodiment, while in mute mode, the device consumes approximately twenty-five percent of the power consumed during normal operation in outside mode or inside mode. In mute mode, the user may manually trigger either of the chirp definitions at any time according to one embodiment of the present invention.

Off mode reduces power used by the power amplifier and several other circuits to conserve power. When in off mode, the device does not chirp. For example, the user may not manually trigger chirps while the device is in off mode. In addition, no automatic chirps are generated while the device is in off mode. The echolocation device may, however, output one or more confirmation tones that occur when accessing control functions according to one embodiment of the present invention. The tones generated while in off mode may not require the use of the power amplifier. It should be appreciated, however, that the echolocation device may not be entirely off, and that while in off mode a tiny amount of power may be consumed. If the power source 86 is a battery or batteries, after a prolonged period of disuse without charging or replacing the battery or batteries, the batteries may self-discharge sufficiently to reset the device.

The Program

The MCU 72 has a non-transitory computer-readable medium that stores program code designed to cause the MCU 72 to execute predetermined commands. When activated, the program will cause the MCU 72 to generate an output signal that will cause the speaker to emit a sound. In one embodiment the sound can be between 9 and 18 kHz. This frequency can be suitable for indoor use. In another embodiment the sound can be between 6 and 12 kHz, a frequency that may be best suited for outdoor use. In either of these modes, the program can optionally cause the MCU 72 to generate a sequence of tones at predetermined time intervals. In one embodiment the time interval is between 3 and 9 seconds. In still another embodiment a user can operate a user interface to send a signal to the MCU 72 that the program interprets to cause the MCU 72 to adjust the time interval.

In addition to controlling the interval between sounds, the program can also cause the MCU 72 to generate a signal that causes the speaker to emit a sound of a predetermined duration. In one embodiment the duration is between 5 and 16 milliseconds. In another embodiment the program causes the MCU 72 to adjust the duration of the tone in response to a signal from the user interface.

In some embodiments the program can control the MCU 72 to generate two or more sounds in sequence, separated by a predetermined delay. Optionally the sounds can be of different frequencies, different amplitudes, or both. Further, the program can optionally cause the MCU 72 to control the delay between tones. In still other embodiments the program can cause the MCU 72 to adjust one or more of the frequencies and amplitudes of the tones and the delay between tones in response to signals from the user interface.

In some embodiments the program can cause the MCU 72 to generate a first tone, wait a predetermined period of time, generate a second tone, wait a predetermined period of time, and then generate a third tone. In one embodiment the first and second tones have the same frequency, and the third tone has a lower frequency.

Optionally input from a user interface can be interpreted by the program to signal the MCU 72 to do one or more of the following: adjust the loudness of the sound, turn the device "on" or "off," mute the output, or place the device in "sleep" mode. It will further be understood that any other functions of the device disclosed herein are implemented by the program.

Command Codes & Functionality

The Braille user interface can optionally be operated according to the following command codes.

In one disclosed embodiment, chirp "A" is triggered by depressing the dot-key on the Braille user interface 84 that corresponds to the letter "A" in Braille, which is dot 1 on the Braille cell interface.

In one disclosed embodiment, chirp "B" is triggered by depressing the dot-keys on the Braille user interface that correspond to the letter "B" in Braille, which is the simultaneous depression of dots 1 and 2.

In one disclosed embodiment, outdoor mode is activated by depressing the dot-keys that correspond to the letter "O" in Braille, which is achieved by simultaneously depressing dots 1, 3, and 5 on the Braille cell interface 84. In one embodiment, the default chirp "A" in outdoor mode has a frequency between 9 kHz and 18 kHz. In some embodiments, the default chirp "A" may be approximately 7 ms in duration and repeat every three seconds with an amplitude of approximately 70 percent. In other embodiments, the default chirp "B" in outdoor mode has a frequency between 6 kHz and 12 kHz. In some embodiments, the default chirp "B" may be approximately 12 ms in duration and repeat every nine seconds with an amplitude of approximately 85 percent.

In one disclosed embodiment, indoor mode is activated by depressing the dot-keys that correspond to the letter "I" in Braille, which corresponds to simultaneously depressing dots 2 and 4 on the Braille cell interface 84. In one embodiment, the default chirp "A" in indoor mode has a frequency between 10 kHz and 20 kHz. In some embodiments, the default chirp "A" may be approximately 6 ms in duration and repeat every four seconds with an amplitude of approximately 70 percent. In other embodiments, the default chirp "B" in indoor mode has a frequency between 6 kHz and 16 kHz. In some embodiments, the default chirp "B" may be approximately 12 ms in duration with an amplitude of approximately 70 percent. In other embodiments, the default chirp "B" does not repeat.

In one disclosed embodiment mute mode is activated by depressing the dot-keys on the Braille cell interface 84 that correspond to the letter "M" in Braille, that is, by simultaneously depressing dots 1, 3, and 4. In some embodiments, mute mode may be toggled with the previous operation mode. In other embodiments, any manually triggered chirps generated while the echolocation device is in mute mode use the chirp definitions from the previous operation mode. In some embodiments, any manually triggered chirps generated while the echolocation device is in mute mode use preset or user-defined chirps. In other embodiments, the device generates a periodic tone while the device is in mute mode. For example, a tone with a frequency of between 10 kHz and 15 kHz may be generated for a duration of 5 ms approximately every 30 seconds with an amplitude of approximately 50 percent.

In one disclosed embodiment, "off" mode is activated by depressing the dot-keys that correspond to the letters "OF" in Braille. Thus, according to one embodiment, off mode is activated by depressing dots 1, 2, 3, 5, and 6 on the Braille cell interface 84. In some embodiments, off mode may be toggled with the previous operation mode. In other embodiments, off mode may be toggled with another particular mode. For example, if the user depresses dots 1, 2, 3, 5, and 6 on the Braille cell interface 84 the device may enter off mode. If the user again depresses dots 1, 2, 3, 5, and 6 on the Braille cell interface 84 the device may toggle to indoor mode. In one embodiment, any chirp settings customized by the user are saved when the device enters off mode. In some embodiments, one or more profiles and/or chirps can be specified by a user.

In one disclosed embodiment, the user may decrease the time between each chirp, thereby making the chirps occur more frequently by depressing the dot-keys that correspond to the letter "F" in Braille, that is, by depressing dots 1, 2, and 4 on the Braille cell interface 84. In one embodiment, the chirp repetition rate is increased by a certain percentage each time dots 1, 2, and 4 are depressed on the Braille cell interface 84. For example, the chirp repetition rate may be increased by 25 percent each time dots 1, 2, and 4 are depressed according to an embodiment. In another embodiment, the repetition rate is increased by a certain amount of time each time dots 1, 2, and 4 are depressed on the Braille cell interface 84. For example, the chirp repetition rate may be increased by 0.5 seconds each time dots 1, 2, and 4 are depressed according to one embodiment.

In one disclosed embodiment, the user may increase the time between each chirp, thereby making the chirps occur less frequently by depressing the dot-keys that correspond to the letter "S" in Braille. Thus, according to one embodiment, the repetition frequency of the chirps may be decreased by depressing dots 2, 3, and 4 on the Braille cell interface 84. In one embodiment, the chirp repetition rate is decreased by a certain percentage each time dots 2, 3, and 4 are depressed on the Braille cell interface 84. For example, the chirp repetition rate may be decreased by 33 percent each time dots 2, 3, and 4 are depressed according to an embodiment. In other embodiment, the repetition rate is decreased by a certain amount of time each time dots 2, 3, and 4 are depressed on the Braille cell interface 84. For example, the chirp repetition rate may be decreased by 0.5 seconds each time dots 2, 3, and 4 are depressed according to one embodiment.

In one disclosed embodiment, the user may increase the volume of a chirp by depressing the dot-keys that correspond to the letter "L" in Braille. Thus, according to one embodiment, the volume of a chirp may be increased by depressing dot keys 1, 2, and 3. In various embodiments of the present invention, depressing dot keys 1, 2, and 3 may change the frequency sweep, duration, and/or amplitude of the chirps. For example, in an embodiment, the frequency sweep is extended by 1 kHz. In another embodiment, the duration may be increased by a specified amount of time, for example, 1 ms. In addition, the amplitude may be increased by a specified amount or a specified percentage, for example, 5 percent. In one embodiment, chirps "A" and "B" are changed according to the same specifications. For example, chirp "A" and chirp "B" may both be increased by 1 ms in duration. In other embodiments, chirps "A" and "B" are changed according to different specifications. For example, chirp "A" may be increased by 1 ms in duration while the frequency of chirp "B" may be changed from 12 kHz to 4 kHz.

In one embodiment of the present invention, the user may decrease the volume of a chirp by depressing the dot-keys that correspond to the letter "Q" in Braille. Thus, according to one embodiment, the volume of a chirp may be decreased by depressing dot keys 1, 2, 3, 4, and 5. In various embodiments of the present invention, depressing dot keys 1, 2, 3, 4, and 5 may change the frequency sweep, duration, and/or amplitude of the chirps. For example, in an embodiment, the frequency sweep is decreased by 1 kHz. In another embodiment, the duration may be decreased by a specified amount of time, for example, 1 ms. In addition, the amplitude may be decreased by a specified amount or a specified percentage, for example, 5 percent. In one embodiment, chirps "A" and "B" are changed according to the same specifications. For example, chirp "A" and chirp "B" may both be decreased by 1 ms in duration. In other embodiments, chirps "A" and "B" are changed according to different specifications. For example, chirp "A" may be decreased by 1 ms in duration while the frequency of chirp "B" may be changed from its current setting to the default setting for that mode.

In one embodiment of the present invention, the user may reset chirp "A" to preset levels by depressing the dot-keys that correspond to the letter "X" in Braille. Thus, according to one embodiment, chirp "A" may be reset to its default values by depressing dot keys 1, 3, 4, and 6.

In one embodiment of the present invention, the user may reset chirp "B" to preset levels by depressing the dot-keys that correspond to the letter "Y" in Braille. Thus, according to one embodiment, chirp "B" may be reset to its default values by depressing dot keys 1, 3, 4, 5, and 6.

In one embodiment of the present invention, the user may reset chirps "A" and "B" to preset levels by depressing the dot-keys that correspond to the letter "Z" in Braille. Thus, according to one embodiment, chirps "A" and "B" may be reset to their default values by depressing dot keys 1, 3, 5, and 6. In an embodiment, a default setting for one chirp may be different than a default setting for another chirp. For example, a default volume for chirp A may be lower than a default volume for chirp B. In one embodiment, a user may depress a dot-key that corresponds to a particular shortcut, such as a manual flash trigger, an increase or decrease in repetition rate, an increase or decrease in volume, etc. For example, a user may depress dot key 1 to manually trigger a flash. As another example, a user may depress dot key 2 to decrease repetition rate or dot key 3 to increase repetition rate. In one embodiment, a user can depress dot key 5 to decrease volume or depress dot key 6 to increase volume. Volume may controlled via adjustments to signal amplitude, duration, and/or mean sweep frequency, such as by lowering frequency sweep. For example, in an embodiment, a tone burst at a particular volume may have a particular amplitude, one or more particular frequencies, and a particular duration. In this embodiment, if the volume is increased, then the tone burst may have a greater amplitude, one or more lower frequencies, and a longer duration. Thus, in embodiments, a change in volume corresponds to a change in acoustic energy which can include a change in amplitude, one or more frequencies, and/or duration. In embodiments, aspects of one or more chirps may change together or independently from one or more other chirps. For example, in one embodiment, when the volume is changed, the amplitude of a first chirp is changed and the amplitude and frequency of a second chirp is changed. Numerous other embodiments are disclosed herein and variations are within the scope of this disclosure.

The foregoing examples of command codes are optional, and other Braille letters or numbers can be used to activate the various features of the device if a Braille cell user interface is selected.

Finally, it will be understood that the preferred embodiment has been disclosed by way of example, and that other modifications may occur to those skilled in the art without departing from the scope and spirit of the appended claims.

Example Method

Figure 9:
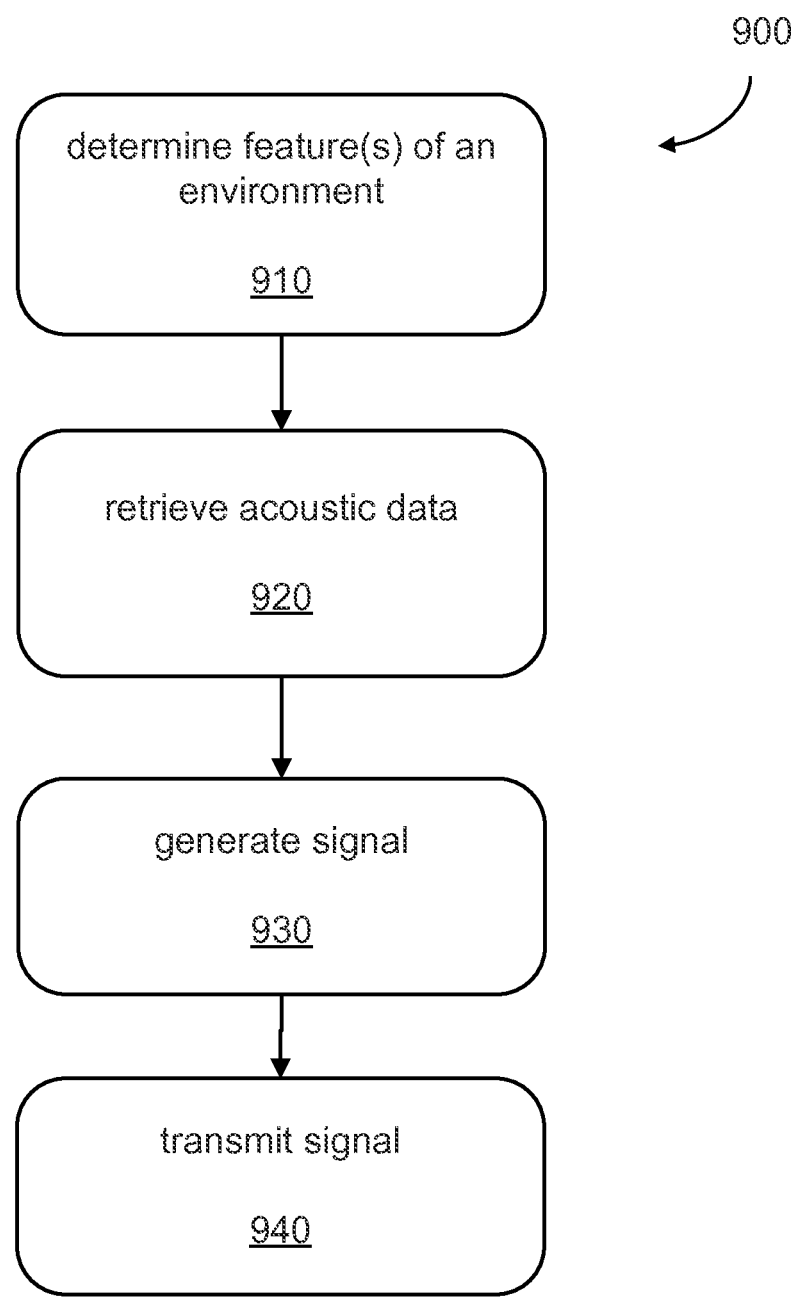
FIG. 9 is a flow chart directed to a method of generating sound waves according to one embodiment of the present invention.

Referring now to FIG. 9, this figure is directed to a method 900 of generating sound waves according to one embodiment of the present invention. For example, method 900 may be implemented for creating sounds to echo off objects in an environment such that an unsighted person can hear the echoes and use them to assist in navigation. In embodiments, at least a portion of method 900 can be performed by one or more electronic devices, such as an echolocation device shown in FIG. 3.

The method 900 begins in block 910 when one or more features of an environment are determined. In one embodiment, one or more features of an environment are determined based at least in part on input received from a user. For example, a user of an echolocation device may select an indoor environment or an outdoor environment by providing input, such as pressing a button on an echolocation device. In other embodiments, one or more features of an environment are determined based at least in part on input received from one or more sensors. For example, a microphone associated with an echolocation device may be used to determine the time it takes for an echo to be received by the echolocation device. In this embodiment, the electronic device may use the determined time to determine an environment. As another example, an echolocation location may determine whether a user is standing still, walking, riding a bicycle, or otherwise moving. In embodiments, there may be any number of environments that can be dynamically determined and/or selected by a user. For example, in one embodiment, an echolocation device can dynamically determine whether the device is located in an indoor environment or whether the device is in an outdoor environment. As another example, a user of the echolocation device may be able to select the environment as being indoor or outdoor. In other embodiments, there may be two, three, four, or more environments from which a suitable environment can be dynamically determined or otherwise selected. Various predetermined and/or user provided settings, including but not limited to, tones, frequency, sweep ranges, timing, etc., may be specified for each environment. Numerous other embodiments are disclosed herein and variations are within the scope of this disclosure.

Once one or more features of an environment have been determined 910, the method 900 proceeds to block 920. In block 920, acoustic data is received. For example, acoustic data may be received from memory associated with an echolocation device. In embodiments, the acoustic data corresponds to one or more sounds for use in creating echoes suitable for use in the environment. For example, the received acoustic data may correspond to one or more of the determined features of the environment. As another example, the received acoustic data may correspond to one or more sounds for an environment determined at least in part on the one or more features. Thus, in an embodiment, the electronic device correlates one or more of the determined features with a suitable environment and receives or otherwise retrieves one or more sounds that are suitable for the environment. Numerous other embodiments are disclosed herein and variations are within the scope of this disclosure.

Once acoustic data has been received 920, the method 900 proceeds to block 930. In block 930, one or more transducer signals are generated. In embodiments, one or more transducer signals are generated based at least in part on the received acoustic data. For example, if the received acoustic data indicates that a sound wave having a particular frequency should be output by an echolocation device, then a transducer signal configured to cause a transducer to output a sound wave having the particular frequency can be generated. As another example, if the received acoustic data indicates that a series of sounds having a downward or upward sweep should be output by an echolocation device, then a series of transducer signals configured to cause the transducer to output a series of sounds having a downward or upward sweep may be generated. Numerous other embodiments are disclosed herein and variations are within the scope of this disclosure.

Once one or more transducer signals have been generated 930, the method 900 proceeds to block 940. In block 940, one or more transducer signals are transmitted to one or more transducers. For example, an echolocation device may transmit a generated transducer signal to a transducer in the echolocation device. In this embodiment, the transducer converts the transducer signal into acoustic energy. For example, the transducer may convert the transducer signal into a sound wave having a particular frequency. In embodiments, the frequency of the sound wave output by the transducer corresponds to a determined frequency based at least in part on the determined features of an environment, a determined environment, and/or received acoustic data. transmitting the transducer signal to a transducer in order to convert the transducer signal into acoustic energy. Numerous other embodiments are disclosed herein and variations are within the scope of this disclosure.

General

While the methods and systems herein are described in terms of software executing on various machines, the methods and systems may also be implemented as specifically-configured hardware, such as field-programmable gate array (FPGA) specifically to execute the various methods. For example, embodiments can be implemented in digital electronic circuitry, or in computer hardware, firmware, software, or in a combination thereof. In one embodiment, a device may comprise a processor or processors. The processor comprises a computer-readable medium, such as a random access memory (RAM) coupled to the processor. The processor executes computer-executable program instructions stored in memory. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

Reference herein to "one embodiment" or "an embodiment" means that a particular feature, structure, operation, or other characteristic described in connection with the embodiment may be included in at least one implementation of the invention. The invention is not restricted to the particular embodiments described as such. The appearance of the phrase "in one embodiment" or "in an embodiment" in various places in the specification does not necessarily refer to the same embodiment. Any particular feature, structure, operation, or other characteristic described in this specification in relation to "one embodiment" may be combined with other features, structures, operations, or other characteristics described in respect of any other embodiment.

What is claimed is:

1. A device for creating sounds to echo off objects in environments such that an unsighted person can hear the echoes and use them to assist in navigation, the device comprising:
    a user interface configured to receive an input corresponding to a selection of a first environment or a second environment larger than the first environment
    a central processing unit configured to receive the input corresponding to the selection of the first environment or the second environment;
    a first memory operatively associated with the central processing unit and having stored therein first data corresponding to a first sound for use in creating echoes suitable for use in the first environment;
    a second memory operatively associated with the central processing unit and having stored therein second data corresponding to a second sound for use in creating echoes suitable for use in the second environment, wherein the first sound is different than the second sound;
    a transducer operatively associated with the central processing unit for converting electrical energy into acoustic energy; and
    wherein the central processing unit is further configured to:
        determine whether to use the first environment or the second environment based at least in part on the input;
        recall the first data, generate a first electrical output signal configured to cause the transducer to emit a first tone corresponding to the first sound based at least in part on the first data, and output the first electrical output signal to the transducer, if the central processing unit determines to use the first environment; and
        recall the second data, generate a second electrical output signal configured to cause the transducer to emit a second tone corresponding to the second sound based at least in part on the second data, and output the second electrical output signal to the transducer, if the central processing unit determines to use the second environment.

2. The device of claim 1, wherein the first environment is an indoor environment and the second environment is an outdoor environment.

3. The device of claim 1, wherein the first tone is configured to allow direct hearing of echoes off objects in the first environment to assist navigation in the first environment, and wherein the second tone is configured to allow direct hearing of echoes off objects in the second environment to assist navigation in the second environment.

4. The device of claim 3, wherein the device does not comprise a receiving transducer.

5. The device of claim 1, wherein the first sound comprises a frequency between 10 kilohertz and 20 kilohertz.

6. The device of claim 1, wherein the second sound comprises a frequency between 6 kilohertz and 12 kilohertz.

7. The device of claim 1, wherein at least one of the first tone or the second tone comprises a sine wave.

8. The device of claim 7, wherein at least one of the first tone or the second tone comprises a single frequency.

9. The device of claim 1, wherein at least one of the first tone or the second tone comprises a square wave.

10. The device of claim 1, wherein at least one of the first tone or the second tone comprises a plurality of tones.

11. The device of claim 10, wherein the plurality of tones correspond with a series of sounds in a downward sweep or an upward sweep.

12. The device of claim 11, wherein the plurality of tones that correspond with the series of sounds are tailored based at least in part on a type of activity.

13. The device of claim 11, wherein the series of sounds correspond with a frequency range corresponding to an octave.

14. The device of claim 1, wherein the first sound corresponds with a first set of tones alternating between at least the first tone and a third tone, wherein the second sound corresponds with a second set of tones alternating between at least the second tone and a fourth tone, wherein a first range of frequencies corresponding to the first tone and third tone is higher than a second range of frequencies corresponding to the second tone and fourth tone.

15. The device of claim 1, wherein the user interface comprises a Braille cell interface.

16. The device of claim 15, wherein the user interface is further configured to receive input configured to control a volume corresponding to at least one of the first sound or the second sound.

17. The device of claim 16, wherein a change in the volume corresponds to a change in an amplitude, a duration, and a frequency corresponding to at least one of the first sound or the second sound.

18. The device of claim 1, wherein the user interface is remote from the central processing unit and communicates wirelessly with the central processing unit.

19. The device of claim 18, wherein the user interface is a Braille cell interface configured to be mounted to an object.

20. The device of claim 19, wherein the object is a cane, a cap, or a headband.

21. The device of claim 19, wherein the Braille cell interface is sized to be carried in a user's pocket.

22. A method for creating sounds to echo off objects in environments such that an unsighted person can hear the echoes and use them to assist in navigation, the method comprising:
- receiving, by a central processing unit, an input from a user interface, the input corresponding to a selection of a first environment or a second environment larger than the first environment
- determining, by the central processing unit, whether to use the first environment or the second environment based at least in part on the input;
- if the central processing unit determines to use the first environment, generating, by the central processing unit, a first electrical output signal configured to cause a transducer to emit a first tone corresponding to a first sound for use in creating echoes suitable for use in the first environment;
- if the central processing unit determines to use the second environment, generating, by the central processing unit, a second electrical output signal configured to cause the transducer to emit a second tone corresponding to a second sound for use in creating echoes suitable for use in the second environment, the second sound different from the first sound; and
- outputting, by the central processor unit, the first electrical output signal or the second electrical output signal to the transducer.

\* \* \* \* \*